(12) United States Patent
Sado et al.

(10) Patent No.: US 8,586,199 B2
(45) Date of Patent: Nov. 19, 2013

(54) ORGANIC ELECTROLUMINESCENCE DEVICE

(75) Inventors: Takayasu Sado, Chiba (JP); Kiyoshi Ikeda, Chiba (JP); Kenichi Fukuoka, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 912 days.

(21) Appl. No.: 12/098,095

(22) Filed: Apr. 4, 2008

(65) Prior Publication Data

US 2008/0290795 A1 Nov. 27, 2008

(30) Foreign Application Priority Data

Apr. 6, 2007 (JP) ................................. 2007-100849

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 585/26; 585/27

(58) Field of Classification Search
USPC ............. 428/690; 313/504, 505, 506; 257/40, 257/E51.05, E51.026, E51.032; 585/26, 27
See application file for complete search history.

(56) References Cited

U.S. PATENT DOCUMENTS

| | | | |
|---|---|---|---|
| 6,531,234 B1 * | 3/2003 | Higashi et al. | 428/690 |
| 6,617,051 B1 | 9/2003 | Higashi et al. | |
| 2003/0027016 A1 * | 2/2003 | Ara et al. | 428/690 |
| 2004/0007971 A1 | 1/2004 | Higashi et al. | |
| 2005/0127827 A1 | 6/2005 | Hiraoka et al. | |
| 2007/0054148 A1 | 3/2007 | Matsuo et al. | |

FOREIGN PATENT DOCUMENTS

| | | |
|---|---|---|
| JP | 10-255972 | 9/1998 |
| JP | 11-92915 | 4/1999 |
| JP | 2000-100566 | 4/2000 |
| JP | 3290432 | 3/2002 |
| JP | 2002-97465 | 4/2002 |
| JP | 2002-175885 | 6/2002 |
| JP | 2002-338377 | 11/2002 |

(Continued)

OTHER PUBLICATIONS

Dodge et. al., Regioselective Synthesis . . . , 1990, J. Org. Chem., vol. 55, pp. 4190-4198.*

(Continued)

*Primary Examiner* — Gregory Clark
(74) *Attorney, Agent, or Firm* — Oblon, Spivak, McClelland, Maier & Neustadt, L.L.P.

(57) ABSTRACT

Provided is an organic electroluminescence device in which a reduction in luminance is suppressed and a lifetime is significantly improved. The object is achieved by an organic electroluminescence device having organic compound layers including an organic emitting layer, which is interposed between at least one pair of electrodes, in which the organic emitting layer is formed of an organic compound material containing an impurity composed of a hydroxyl group-containing compound at a concentration of less than 0.15% by mass, and a method of selecting an organic compound material for the organic electroluminescence device, the method including: determining the content of the impurity; and selecting an organic compound material in which the content is less than 0.15% by mass so that the material is used for forming the organic emitting layer. Provided are a coating film-forming ink, a method of forming a thin film, and a method of producing an organic electroluminescence device.

4 Claims, 3 Drawing Sheets

(56) References Cited

FOREIGN PATENT DOCUMENTS

| | | |
|---|---|---|
| JP | 2002-373785 | 12/2002 |
| JP | 2003-338377 * | 11/2003 |
| JP | 2004-311415 | 11/2004 |
| JP | 2004-327454 | 11/2004 |
| JP | 2005-11732 | 1/2005 |
| JP | 2005-150099 | 6/2005 |
| JP | 2005-174845 | 6/2005 |
| JP | 2006-236629 | 9/2006 |
| WO | WO 00/41443 | 7/2000 |
| WO | WO 2005/014551 A1 | 2/2005 |

OTHER PUBLICATIONS

English Translation of JP 2003-338377.*
U.S. Appl. No. 12/044,291, filed Mar. 7, 2008, Hosokawa, et al.
U.S. Appl. No. 12/044,436, filed Mar. 7, 2008, Hosokawa, et al.
U.S. Appl. No. 11/839,949, filed Aug. 16, 2007, Jinde, et al.
U.S. Appl. No. 12/280,475, filed Oct. 1, 2008, Ikeda, et al.

* cited by examiner

ORGANIC ELECTROLUMINESCENCE DEVICE

TECHNICAL FIELD

The present invention relates to an organic electroluminescence device and a method of selecting an organic compound material, and more specifically, to an organic electroluminescence device in which the concentration of an impurity composed of a hydroxyl group-containing compound in an organic compound material of which an organic emitting layer is constituted is reduced so as to be equal to or lower than a certain numerical value and a method of selecting the organic compound material.

BACKGROUND ART

Since an organic electroluminescence device (hereinafter, electroluminescence sometimes abbreviated as "EL") of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on devices using organic materials as the constituting materials. An organic EL device is an emitting device having at least an organic emitting layer interposed between at least one pair of electrodes. The organic EL device is a spontaneous emitting device that utilizes the following principle: a fluorescent substance emits light with the recombination energy of a hole injected from an anode and an electron injected from a cathode when an electric field is applied to the substance. The organic EL device has various characteristics including the following ones: the device can emit light with high efficiency, is available at a low cost, and has a light weight and a small thickness.

The following phenomenon has been known as a problem inherent in the organic EL device: the luminance of the device reduces over time in association with the driving of the device. Various improvements have been attempted to suppress the reduction in luminance.

One known cause for the reduction in luminance is the presence of various impurities included in organic compound layers including the organic emitting layer as a component for the organic EL device, and the following attempt has been reported: the emission half lifetime of the organic EL device is improved by reducing the amounts of the impurities.

Examples of the impurities include: an impurity included at the time of the washing of the substrate of the organic EL device (see Patent Document 1); an impurity such as adsorbed water vapor or an adsorbed gas (see Patent Document 2); a halogen-containing compound (see Patent Documents 3 to 5); a substituted carbazole compound having an amino group (see Patent Document 6); a metal ion (see Patent Document 7); and a solvent having a large dipole moment (see Patent Document 8).

None of the above respective reports discloses that the emission half lifetime of the organic EL device reduces when even a trace amount of a compound having a hydroxyl group, in particular, a hydroxyl group-containing compound as a precursor or by-product which: has substantially the same basic skeleton as that of an organic compound material of which the organic emitting layer is constituted; and is expected to function as an organic compound for the device is included as an impurity and that the emission half lifetime is improved by reducing the amount of such impurity.

In particular, the hydroxyl group-containing compound as a precursor or by-product has a structure similar to that of the organic compound material. Accordingly, it is often difficult to separate the hydroxyl group-containing compound from the organic compound material to purify the organic emitting layer, and no attention has been paid to the hydroxyl group-containing compound despite the potential of the compound to serve as an impurity that adversely affects the emission half lifetime.

An influence of such impurity will be specifically described below. Upon synthesis of an organic compound for an organic EL device, a hydroxyl group remains in the compound in some cases. When a synthesis route for the compound includes the step of producing a compound containing a hydroxyl group as a precursor, the final reaction compound inevitably contains a considerable amount of a hydroxyl group-containing compound as a precursor as it is or as a by-product. Once the hydroxyl group-containing compound as a precursor or by-product is included in the main product, there arises the following problem: the hydroxyl group-containing compound cannot be easily removed unless the compound is intentionally removed because the compound and the main product have the same skeleton structure or similar skeleton structures. The inventors of the present invention have made extensive studies, and, as a result, have found that a hydroxyl group-containing impurity out of multiple possible impurities extremely affects the emission lifetime of the organic EL device. When a hydroxyl group-containing compound is produced as a precursor or by-product for the convenience of the synthesis route, the final reaction compound contains a large amount of the hydroxyl group-containing compound, so the problem becomes remarkable.

Here, in a technique of an organic EL field, the presence of an impurity and the performance of a device are complicatedly related to each other. For example, the following story behind the fact that an organic EL technique has reached a practical level is well known: the luminous efficiency and lifetime of an organic EL device are drastically improved by doping a host material with a specific impurity. However, even in such doping technique, when the concentration at which the host material is doped with the impurity deviates from an optimum range, the concentration quenching of the device or the deterioration of the lifetime of the device occurs. On the other hand, the presence of a certain kind of an impurity is known to exert, for example, the following adverse effect: the impurity deteriorates the color purity of the device, increases the voltage at which the device is driven, or deteriorates the lifetime of the device.

Although it has been known that, as described above, the addition or removal of a certain kind of an impurity is important in the organic EL field, it is extremely laborious and extremely costly to manage the concentrations of all impurities that may be present appropriately, and the management has presented a large obstacle to the full-fledged commercialization of organic EL devices. In the present invention, an OH group-containing compound was specified as a target specific impurity the concentration of which was to be controlled.

[Patent Document 1] JP 10-255972 A
[Patent Document 2] JP 11-92915 A
[Patent Document 3] WO 00/041443 (JP 3290432 A)
[Patent Document 4] JP 2002-175885 A
[Patent Document 5] JP 2004-327454 A
[Patent Document 6] JP 2004-311415 A
[Patent Document 7] JP 2005-150099 A
[Patent Document 8] JP 2006-236629 A

DISCLOSURE OF THE INVENTION

Problems to be Solved by the Invention

In view of such circumstances, an object of the present invention is to lengthen the lifetime of an organic EL device by controlling the concentration of a hydroxyl group-containing compound in an organic compound material of which the organic EL device is constituted.

Means for Solving the Problems

The inventors of the present invention have made extensive studies with a view to achieving the above object. As a result, the inventors have found that the object can be achieved by reducing the amount of an impurity, that is, a compound having a hydroxyl group, in particular, a hydroxyl group-containing compound as a precursor for, or a by-product of, an organic compound material of which an organic emitting layer is constituted to be included in the material. The present invention has been completed based on the finding described above.

That is, the present invention provides the following items (1) to (17):

(1) an organic electroluminescence device including organic compound layers including an organic emitting layer, the organic compound layers being interposed between at least one pair of electrodes, in which the organic emitting layer is formed of organic compound materials each containing a hydroxyl group-containing compound at a content of less than 0.15% by mass;

(2) an organic electroluminescence device according to the above item (1), in which the hydroxyl group-containing compound includes a precursor for, or a by-product of, each of the organic compound materials;

(3) an organic electroluminescence device according to the above item (1) or (2), in which the hydroxyl group-containing compound includes a diol compound;

(4) an organic electroluminescence device according to the above item (1) or (2), in which the organic compound materials include at least one selected from a phenanthroline derivative, a triphenyldiamine derivative, a stilbene derivative, a coumarin derivative, a tetraphenylbutadiene derivative, an anthrylarylene derivative, a distyrylarylene derivative, a tristyrylarylene derivative, an oligoarylene derivative, a phenylanthracene derivative, a bisanthracene derivative, a p-polyphenylenevinylene derivative, a polyfluorene derivative, an aminodibenzofluorene derivative, a benzothiadiazole derivative, a carbazole derivative, a diaminopyrene derivative, a silane cyclopentadiene derivative, a bianthryl derivative, a naphthacene-based compound, an anthracene-based compound, a tetracene-based compound, nitrogen-containing heterocyclic compounds including a pyrazine compound, a quinoline compound, and a quinoxaline compound, a nitrogen-containing heterocyclic compound, a spiro bond-containing compound, an arylamine-based compound, a fluoranthene skeleton-containing compound, an aromatic dimethylidyne-based compound, an aromatic oligoamine derivative, a fused aromatic hydrocarbon-substituted biphenyl derivative, a benzothiophene derivative, a dibenzotriphenylene derivative, an amine-containing monostyryl derivative, and amine-containing polystyryl derivatives including an amine-containing distyryl derivative, an amine-containing tristyryl derivative, and an amine-containing tetrastyryl derivative;

(5) an organic electroluminescence device according to the above item (1) or (2), in which the organic compound materials each include a naphthacene derivative represented by the following formula (1):

[Chemical formula 1]

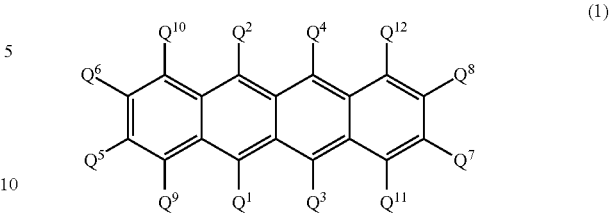

(1)

where $Q^1$ to $Q^{12}$ each independently represent a hydrogen atom, a substituted or unsubstituted alkyl group having 1 to 20 carbon atoms, a substituted or unsubstituted aryl group having 6 to 30 carbon atoms, a substituted or unsubstituted amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 30 carbon atoms, a substituted or unsubstituted arylthio group having 6 to 30 carbon atoms, a substituted or unsubstituted alkenyl group having 1 to 20 carbon atoms, a substituted or unsubstituted aralkyl group having 7 to 30 carbon atoms forming an aromatic ring, or a substituted or unsubstituted heterocyclic group, and $Q^1$ to $Q^{12}$ may be identical to or different from one another;

(6) an organic electroluminescence device according to the above item (5), in which at least one of $Q^1$, $Q^2$, $Q^3$, and $Q^4$ represent a substituted or unsubstituted aryl group having 6 to 30 carbon atoms;

(7) an organic electroluminescence device according to the above item (6), in which the naphthacene derivative represented by the formula (1) is represented by the following formula (2):

[Chemical formula 2]

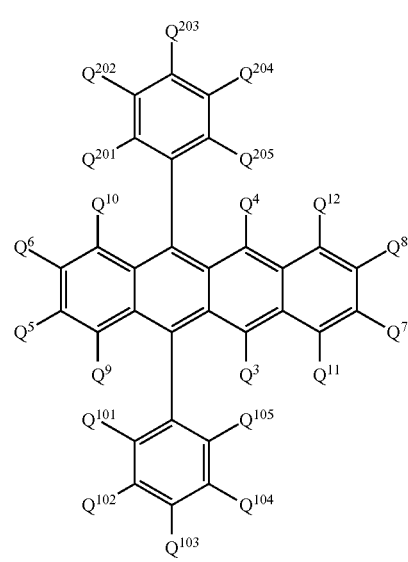

(2)

where $Q^3$ to $Q^{12}$, $Q^{101}$ to $Q^{105}$, and $Q^{201}$ to $Q^{205}$ each independently represent the same group as that represented by any one of $Q^3$ to $Q^{12}$ in the general formula (1), and $Q^3$ to $Q^{12}$, $Q^{101}$ to $Q^{105}$ and $Q^{201}$ to $Q^{205}$ may be identical to or different from one another, or two or more adjacent groups of $Q^3$ to $Q^{12}$, $Q^{101}$ to $Q^{105}$ and $Q^{201}$ to $Q^{205}$ may be bonded to each other to form a ring;

(8) an organic electroluminescence device according to the above item (7), in which at least one of $Q^{101}$, $Q^{105}$, $Q^{201}$, and $Q^{205}$ in the naphthacene derivative represented by the formula (2) represent a substituted or unsubstituted alkyl group, a substituted or unsubstituted aryl group, a substituted or unsubstituted amino group, a substituted or unsubstituted alkoxy group, a substituted or unsubstituted aryloxy group, a substituted or unsubstituted alkylthio group, a substituted or unsubstituted arylthio group, a substituted or unsubstituted alkenyl group, a substituted or unsubstituted aralkyl group, or a substituted or unsubstituted heterocyclic group, and $Q^{101}$, $Q^{105}$, $Q^{201}$, and $Q^{205}$ may be identical to or different from one another;

(9) an organic electroluminescence device according to the above item (1) or (2), in which the organic compound layers are constituted of a hole injecting layer, a hole transporting layer, the organic emitting layer, and an electron injecting layer;

(10) an organic electroluminescence device according to the above item (1) or (2), in which an organic compound material purified by a sublimation method is used as at least one of the organic compound materials of which the organic emitting layer is formed;

(11) an organic electroluminescence device according to the above item (1) or (2), in which an organic compound material purified by one of a recrystallization method, a reprecipitation purification method, and a combination of the recrystallization method and the reprecipitation crystallization method is used as at least one of the organic compound materials of which the organic emitting layer is formed;

(12) a method of selecting an organic compound material for an organic electroluminescence device, the method including: determining a content of an impurity composed of a hydroxyl group-containing compound in at least one organic compound material of which an organic emitting layer is to be formed; and selecting an organic compound material in which the content is less than 0.15% by mass so that the material is used for forming the organic emitting layer;

(13) a method of selecting an organic compound material for an organic electroluminescence device according to the above item (12), in which the content of the impurity composed of the hydroxyl group-containing compound in the at least one organic compound material is determined by a high performance liquid chromatography method;

(14) a coating film-forming ink for an organic electroluminescence device, including: at least one of the organic compound materials according to any one of the above items (1) to (8); and an organic solvent;

(15) a method of forming a thin film, the method being characterized by including: applying the coating film-forming ink according to the above item (14) onto a substrate by a wet method; and drying the applied ink under heat to form the ink into a thin film;

(16) a method of producing an organic electroluminescence device, the method being characterized by interposing a substrate obtained by the method of forming a thin film according to the above item (15) between an anode and a cathode; and

(17) an organic electroluminescence device produced by the method according to the above item (16).

Effects of the Invention

According to the present invention, a reduction in luminance of an organic EL device is suppressed and the lifetime of the device is significantly improved by reducing the content of a specific compound as an impurity.

To be additionally specific, the lifetime of the device can be lengthened by controlling the concentration of a hydroxyl group-containing impurity to a predetermined value, that is, less than 0.15% by mass; the lifetime can be lengthened by controlling the concentration of the hydroxyl group-containing impurity to preferably 0.001 to 0.15% by mass.

According to the present invention, the lifetime of an organic EL device can be innovatively lengthened with a small number of steps at a low cost by managing and reducing the concentration of a specific impurity which: may be included in a large amount in a main product for the convenience of, for example, a synthesis route for an organic compound for the device; and has a remarkable influence on the lifetime of the device.

BEST MODE FOR CARRYING OUT THE INVENTION

Figure 1:
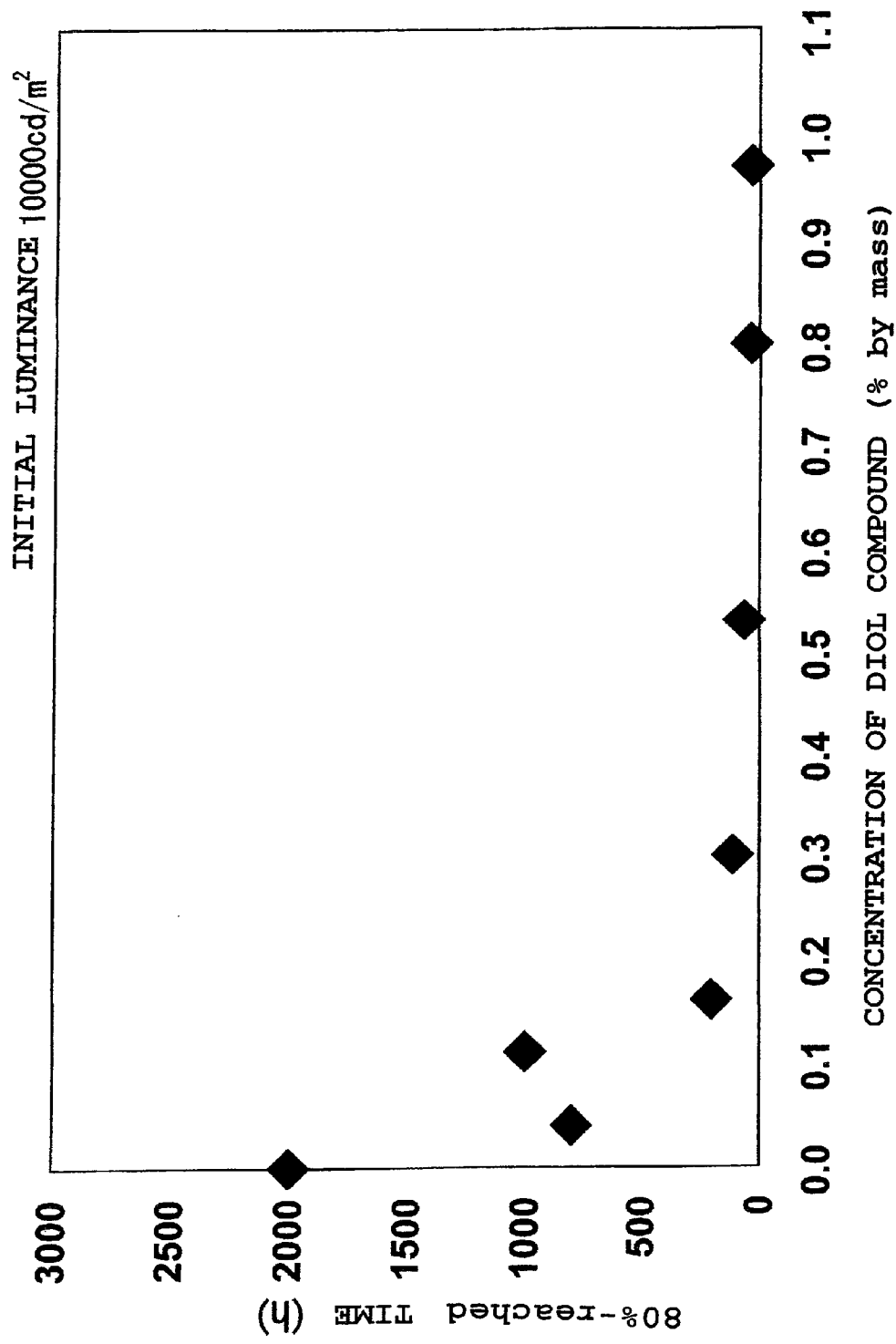
FIG. 1 is a graph obtained by plotting the time period for which each of organic EL devices obtained in Examples 1 to 3 and Comparative Examples 1 to 5 is driven so that the luminance of the device reaches 80% of an initial luminance of 10,000 cd/m² (80%-reached time).

In the present invention, an organic compound material of which an organic emitting layer is constituted is not particularly limited.

To be specific, the organic compound materials include a phenanthroline derivative, a triphenyldiamine derivative, a stilbene derivative, a coumarin derivative, a tetraphenylbutadiene derivative, an anthrylarylene derivative, a distyrylarylene derivative, a tristyrylarylene derivative, an oligoarylene derivative, a phenylanthracene derivative, a bisanthracene derivative, a p-polyphenylenevinylene derivative, a polyfluorene derivative, an aminodibenzofluorene derivative, a benzothiadiazole derivative, a carbazole derivative, a diaminopyrene derivative, a silane cyclopentadiene derivative, a bianthryl derivative, a naphthacene-based compound, an anthracene-based compound, a tetracene-based compound, nitrogen-containing heterocyclic compounds including a pyrazine compound, a quinoline compound, and a quinoxaline compound, a nitrogen-containing heterocyclic compound, a spiro bond-containing compound, an arylamine-based compound, a fluoranthene skeleton-containing compound, an aromatic dimethylidyne-based compound, an aromatic oligoamine derivative, a fused aromatic hydrocarbon-substituted biphenyl derivative, a benzothiophene derivative, a dibenzotriphenylene derivative, an amine-containing monostyryl derivative, and amine-containing polystyryl derivatives including an amine-containing distyryl derivative, an amine-containing tristyryl derivative, and an amine-containing tetrastyryl derivative.

The hydroxyl group-containing compound as an impurity in the present invention means a compound containing a hydroxyl group in a precursor for, or a by-product of, any one of the listed organic compound materials.

A precursor for, for example, a tetracene compound represented by the formula (1) out of the listed organic compound materials is a compound represented by the following formula (B-1). A by-product of the compound represented by the formula (1) is, for example, a compound represented by the following formula (B-2) or (B-3)

[Chemical formula 3]

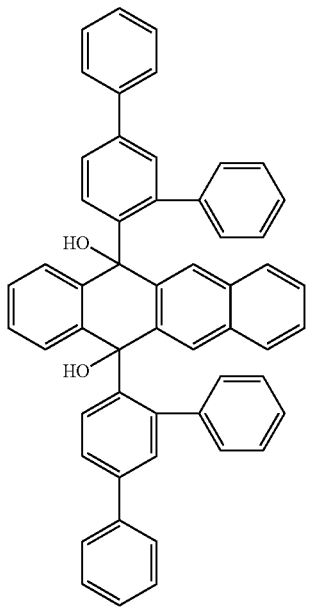

(B-1)

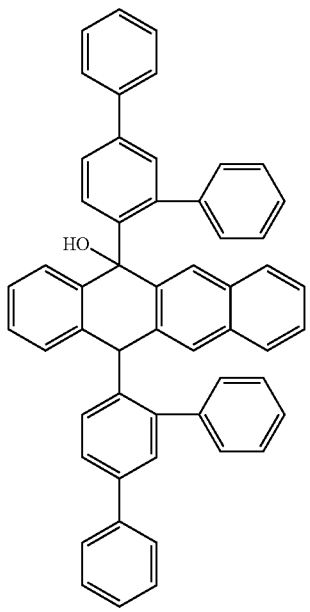

(B-2)

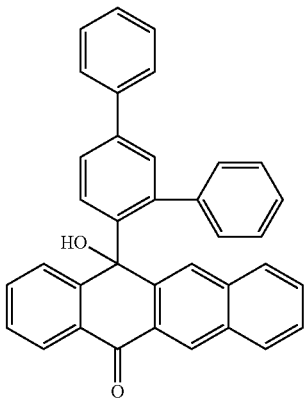

(B-3)

In the present invention, the concentration of the hydroxyl group-containing compound must be less than 0.15% by mass. The concentration of the hydroxyl group-containing compound is more preferably 0.001 to 0.15% by mass. Setting the concentration of the hydroxyl group-containing compound to less than 0.15% by mass can prevent the lifetime of the organic EL device from reducing.

The concentration of the hydroxyl group-containing compound in the present invention can be analyzed by, for example, an infrared absorption method, a gas chromatography-flame ionization detection (FID) method, gas chromatography-mass spectrometry, a high performance liquid chromatography-differential refractometer method, a high performance liquid chromatography-ultraviolet absorptiometer method, or a high performance liquid chromatography-mass spectrometry.

A method of purifying any one of the listed organic compound materials is, for example, a sublimation purification method, a recrystallization method, a reprecipitation purification method, a combination of the recrystallization method and the reprecipitation purification method, a zone melting method, a column purification method, or an adsorption method. Of those, the sublimation purification method is preferably applied because basically no solvent is used in the method.

However, even in a purification method in which basically no solvent is used like the sublimation purification method, a solvent is often used in the final step where an operation is performed when any such organic compound material is in a liquid state, and attention should be paid particularly when a solvent containing a hydroxyl group is used because the solvent may remain in an amount of the order of several parts per million to have a significant influence on the performance of the device.

A solvent to be used in the recrystallization method or the reprecipitation purification method, or in the combination of them is a solvent having a relatively low boiling point such as acetone, methyl ethyl ketone, tetrahydrofuran, methanol, ethanol, propanol, n-hexane, xylene, cyclopropene, cyclohexene, 1,2-butadiene, 1-butene, benzene, or toluene. Of those, a solvent free of a hydroxyl group such as acetone, methyl ethyl ketone, n-hexane, benzene, or toluene is preferably used.

The organic compound layers include the respective layers typified by the organic emitting layer and interposed between the anode and the cathode in the above constitution, and the organic EL device is such that one organic compound layer out of the respective layers of which the organic compound layers of the organic EL device are constituted is formed of an organic compound material containing the hydroxyl group-containing compound at a concentration of less than 0.15% by mass.

The organic emitting layer may be composed only of a host material, or may be composed of a combination of the host material and a doping material. In addition, the doping material may be incorporated into the entirety, or part, of the host material. The doping material may be laminated on, or dispersed in, the host material.

The doping material is used in an amount of typically 0.1 to 50 parts by mass, or preferably 0.5 to 10 parts by mass with respect to 100 parts by mass of the host material. Setting the usage of the doping material within the above range can provide an organic EL device having high efficiency and a long lifetime and being excellent in color purity.

In addition, the present invention provides a method of selecting an organic compound material for an organic electroluminescence device to be used as a material for forming an organic emitting layer.

A high performance liquid chromatography method is preferably adopted in the determination of the concentration of an impurity in the material for forming the organic emitting layer to be used in the organic EL device of the present invention. According to the method, a material suitable for the formation of the organic emitting layer can be selected rapidly and accurately as compared to any other method.

In the high performance liquid chromatography method, a mobile phase is delivered with a high-pressure pump (pressure: about 35 to 50 MPa), so the time period required for the separation of the impurity is short, and hence the concentration can be rapidly determined. In addition, a filler to be used here is excellent in separating performance because all the porous particles of the filler each have a particle diameter as small as about 5 to 10 µm, and a large surface area. In addition, the concentration can be analyzed with high accuracy because the pump can be connected to a high-sensitivity detector. Further, the method is excellent in reproducibility of the determination of the concentration because the mobile phase can be delivered at a constant flow rate. Table 1 shows a representative filler and a representative separation mode in the high performance liquid chromatography method.

TABLE 1

| Separation mode | Separating function | Main filler |
| --- | --- | --- |
| Partition chromatograph method | Solubility | Chemically bonded silica gel Polymer gel, Carbon Chemically bonded porous glass |
| Adsorption chromatograph method | Adsorbing power | Silica gel, Alumina Porous glass, Carbon |
| Ion-exchange chromatograph method | Ion exchangeability | Ion exchangeable polystyrene gel Ion exchangeable chemically bonded silica gel Ion exchangeable hydrophilic polymer gel |
| Size exclusion chromatograph method | Molecular size | Polystyrene gel Hydrophilic polymer gel Chemically bonded silica gel |
| Affinity chromatograph method | Biochemical affinity | Ligand bonded hydrophilic polymer Ligand bonded silica gel |

In the high performance liquid chromatography method, the separation mode, which varies depending on a combination of a stationary phase and the mobile phase, can be arbitrarily selected.

Upon determination of the concentration of the impurity in the material for forming an emitting layer in the method of the present invention, reversed phase chromatography involving the use of octadecyl group chemically bonded silica (ODS) classified into the category of the chemically bonded silica gel of the partition chromatograph method is desirably employed because good separating performance can be obtained. The ODS filler is a representative filler in the high performance liquid chromatography method, and is suitable for a wide variety of compound groups. In addition, in the case of the reversed phase chromatography, polar organic solvents such as methanol, acetonitrile, and tetrahydrofuran and a mixed solvent of two or more of them, and, furthermore, a mixed solvent of any such organic solvent and water can each be used; acetonitrile, or a mixed solvent of acetonitrile and tetrahydrofuran is a particularly preferable solvent.

In addition, an arbitrary detector such as a differential refractometer (RI), an ultraviolet absorptiometer (UV), or a mass spectrometer (MS) can be used in the high performance liquid chromatography method. One should prefer to use the ultraviolet absorptiometer rather than to use the differential refractometer because the ultraviolet absorptiometer has higher detection sensitivity than that of the differential refractometer, provides a baseline having better stability than that of a baseline provided by the differential refractometer, and can detect the impurity with high sensitivity without being affected by the temperature or flow rate of the mobile phase. In addition, the mass spectrometer has higher detection sensitivity than that of each of the two detectors, but is poor in stability of detection sensitivity, reproducibility of the determination of the concentration, and property with which the concentration is determined.

Therefore, the optimum combination of a filler, a solvent, and a detector in the case of the high performance liquid chromatography method is as follows: the concentration is analyzed by reversed phase chromatography using the ODS as the filler and acetonitrile or a mixed solvent of acetonitrile and tetrahydrofuran as the solvent, and an ultraviolet absorptiometer is used as the detector.

[Organic EL Device Constitution]

The organic EL device of the present invention will be described in detail in the following.

The organic EL device of the present invention is constituted of organic composition layers including an organic emitting layer constituted of the listed organic compound materials, the organic compound layers being interposed between at least one pair of electrodes. Typical examples of the constitution of the organic EL device include the following.

(1) An anode/organic emitting layer/cathode;
(2) An anode/hole injecting layer/organic emitting layer/cathode;
(3) An anode/organic emitting layer/electron injecting layer/cathode;
(4) An anode/hole injecting layer/organic emitting layer/electron injecting layer/cathode;
(5) An anode/organic semiconductor layer/organic emitting layer/cathode;
(6) An anode/organic semiconductor layer/electron blocking layer/organic emitting layer/cathode;
(7) An anode/organic semiconductor layer/organic emitting layer/adhesion improving layer/cathode;
(8) An anode/hole injecting layer/hole transporting layer/organic emitting layer/electron injecting layer/cathode;
(9) An anode/insulating layer/organic emitting layer/insulating layer/cathode;

(10) An anode/inorganic semiconductor layer/insulating layer/organic emitting layer/insulating layer/cathode;

(11) An anode/organic semiconductor layer/insulating layer/organic emitting layer/insulating layer/cathode;

(12) An anode/insulating layer/hole injecting layer/hole transporting layer/organic emitting layer/insulating layer/cathode; and

(13) An anode/insulating layer/hole injecting layer/hole transporting layer/organic emitting layer/electron injecting layer/a cathode.

Of the above constitutions, anyone of the constitutions (2), (3), (4), (5), (8), (9) and (11) is preferable.

Hereinafter, a function and the like of each layer in the organic EL device will be described

[Light-Transmissive Substrate]

The organic EL device of the present invention is prepared on a light-transmissive substrate when the organic EL device is a lower surface emission type or a bottom emission type, which emits light from the substrate side. The light-transmissive substrate is the substrate which supports the organic EL device. It is preferable that the light-transmissive substrate has a transmittance of light of 50% or greater in the visible region of 400 to 700 nm and is flat and smooth.

Examples of the light-transmissive substrate include glass plates and polymer plates. Specific examples of the glass plate include plates made of soda-lime glass, glass containing barium and strontium, leadglass, aluminosilicate glass, borosilicate glass, barium borosilicate glass, and quartz. Specific examples of the polymer plate include plates made of polycarbonate, acrylic, polyethylene terephthalate, polyether sulfide, and polysulfone. A TFT substrate on which a TFT for driving has been formed is also permitted.

In addition, in the case of a top surface emission type, or top emission type organic EL device that emits light from its upper portion, a reflecting plate made of an appropriate metal such as aluminum must be provided on the above-mentioned substrate.

[Anode]

The anode in the organic EL device of the present invention has the function of injecting holes into the hole transporting layer or the emitting layer. It is effective that the anode has a work function of 4.5 eV or greater. Examples of the material for the anode used in the present invention include indium tin oxide alloys (ITO), tin oxide (NESA), indium zinc oxide alloys (IZO), gold, silver, platinum, and copper.

Each of those materials can be used alone; an alloy of two or more of those materials, or a material obtained by adding any other element to any one of those materials can also be appropriately selected and used.

The anode can be prepared by forming a thin film of the electrode material described above in accordance with a method such as a vapor deposition method and a sputtering method.

When the organic EL device is a lower surface emission type or a bottom emission type, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 μm and preferably in the range of 10 to 200 nm although the preferable range may be different depending on the used material.

[Emitting Layer]

The emitting layer in the organic EL device has a combination of the following functions:

(i) The injecting function: the function of injecting holes from the anode or the hole injecting/transporting layer and injecting electrons from the cathode or the electron injecting/transporting layer when an electric field is applied;

(ii) The transporting function: the function of transporting injected charges (electrons and holes) by the force of the electric field; and (iii) The emitting function: the function of providing the field for recombination of electrons and holes and leading the emission of light.

However, the easiness of injection may be different between holes and electrons and the ability of transportation expressed by the mobility may be different between holes and electrons. It is preferable that either one of the charges be transferred.

As the method of forming the emitting layer, a conventional method such as the vapor deposition method, the spin coating method and the LB method can be used. It is particularly preferable that the emitting layer be a molecular deposit film.

The molecular deposit film is a thin film formed by deposition of a material compound in the gas phase or a film formed by solidification of a material compound in a solution or in the liquid phase. In general, the molecular deposit film can be distinguished from the thin film formed in accordance with the LB method (the molecular accumulation film) based on the differences in the aggregation structure and higher order structures and functional differences caused by these structural differences.

Further, as disclosed in JP 57-51781 A, the emitting layer can also be formed by dissolving a binder such as a resin and the material compounds into a solvent to prepare a solution, followed by forming a thin film from the prepared solution in accordance with the spin coating method or the like.

In the present invention, an organic compound material of which an organic emitting layer is constituted is not particularly limited.

Specific examples of the organic compound materials include at least one selected from a phenanthroline derivative, a triphenyldiamine derivative, a stilbene derivative, a coumarin derivative, a tetraphenylbutadiene derivative, an anthrylarylene derivative, a distyrylarylene derivative, a tristyrylarylene derivative, an oligoarylene derivative, a phenylanthracene derivative, a bisanthracene derivative, a p-polyphenylenevinylene derivative, a polyfluorene derivative, an aminodibenzofluorene derivative, a benzothiadiazole derivative, a carbazole derivative, a diaminopyrene derivative, a silane cyclopentadiene derivative, a bianthryl derivative, a naphthacene-based compound, an anthracene-based compound, a tetracene-based compound, nitrogen-containing heterocyclic compounds (for example, a pyrazine compound, and a quinoline compound), and a quinoxaline compound, a nitrogen-containing heterocyclic compound, a spiro bond-containing compound, an arylamine-based compound, a fluoranthene skeleton-containing compound, an aromatic dimethylidyne-based compound, an aromatic oligoamine derivative, a fused aromatic hydrocarbon-substituted biphenyl derivative, a benzothiophene derivative, a dibenzotriphenylene derivative, an amine-containing monostyryl derivative, and amine-containing polystyryl derivatives (a distyryl derivative, a tristyryl derivative, and a tetrastyryl derivative).

A preferable example of the organic compound material is a naphthacene-based compound represented by the formula (1).

In the formula (1), $Q^1$ to $Q^{12}$ each independently represent a hydrogen atom, a substituted or unsubstituted alkyl group having 1 to 20 carbon atoms, a substituted or unsubstituted aryl group having 6 to 30 carbon atoms, a substituted or unsubstituted amino group, a substituted or unsubstituted alkoxy group having 1 to 20 carbon atoms, a substituted or unsubstituted alkylthio group having 1 to 20 carbon atoms, a substituted or unsubstituted aryloxy group having 6 to 30 carbon atoms, a substituted or unsubstituted arylthio group having 6 to 30 carbon atoms, a substituted or unsubstituted alkenyl group having 1 to 20 carbon atoms, a substituted or unsubstituted aralkyl group having 7 to 30 carbon atoms forming an aromatic ring, or a substituted or unsubstituted heterocyclic group, and $Q^1$ to $Q^{12}$ may be identical to or different from one another.

In the formula (1), $Q^1$ to $Q^4$ each represent preferably hydrogen, or any one of a substituted or unsubstituted alkyl group having 1 to 20 carbon atoms, a substituted or unsubstituted aryl group having 6 to 30 carbon atoms, a substituted or unsubstituted amino group, a substituted or unsubstituted heterocyclic group, and a substituted or unsubstituted alkenyl group having 1 to 20 carbon atoms, or more preferably the aryl group. In addition, it is particularly preferable that $Q^3$ and $Q^4$ each represent hydrogen, and $Q^1$ and $Q^2$ each represent any one of the above substituents.

In addition, $Q^1$ to $Q^4$, which are preferably identical to one another, may be different from one another.

$Q^5$ to $Q^8$ each represent preferably any one of hydrogen, a substituted or unsubstituted alkyl group having 1 to 20 carbon atoms, a substituted or unsubstituted aryl group having 6 to 30 carbon atoms, a substituted or unsubstituted amino group, a substituted or unsubstituted alkenyl group having 1 to 20 carbon atoms, and a substituted or unsubstituted heterocyclic group, or particularly preferably hydrogen, or a substituted or unsubstituted aryl group having 6 to 30 carbon atoms. In addition, $Q^5$ and $Q^6$, or $Q^7$ and $Q^8$, which are preferably identical to each other, may be different from each other. In addition, $Q^9$ to $Q^{12}$ each preferably represent hydrogen.

The alkyl group represented by any one of $Q^1$ to $Q^{12}$ may have a substituent, and may be linear or branched. Preferable specific examples of the alkyl group include a methyl group, an ethyl group, (n and i)-propyl groups, (m, i, sec, and tert)-butyl groups, and (m, i, neo, and tert)-pentyl groups.

The aryl group represented by any one of $Q^1$ to $Q^{12}$ may be monocyclic or polycyclic, and a fused ring and a ring assembly are also included in the category of the aryl group. The aryl group may have a substituent. Preferable examples of the aryl group represented by any one of $Q^1$ to $Q^{12}$ include a phenyl group, (o-, m-, and p-)tolyl groups, a pyrenyl group, a perylenyl group, a coronenyl group, (1- and 2-)naphthyl groups, an anthryl group, (o-, m-, and p-)biphenylyl groups, a terphenyl group, and a phenanthryl group.

The amino group represented by anyone of $Q^1$ to $Q^{12}$, which may be unsubstituted, preferably has a substituent, and may be any one of, for example, an alkylamino group, an arylamino group, and an aralkylamino group. Each of those groups preferably has an aliphatic hydrocarbon group having 1 to 6 carbon atoms in total and/or an aromatic carbon ring which is monocyclic, bicyclic, tricyclic, or tetracyclic. Specific examples of the amino group include a dimethylamino group, a diethylamino group, a butylamino group, a diphenylamino group, a ditolylamino group, a bisdiphenylamino group, and a bisnaphthylamino group.

The heterocyclic group represented by any one of $Q^1$ to $Q^{12}$ may have a substituent, and is preferably, for example, a five- or six-membered aromatic heterocyclic group containing O, N, or S as a hetero atom or a fused polycyclic aromatic heterocyclic group containing O, N, or S as a hetero atom and having 2 to 20 carbon atoms. Examples of the aromatic heterocyclic group and the fused polycyclic aromatic heterocyclic group include a thienyl group, a furyl group, a pyrrolyl group, a pyridyl group, a quinolyl group, and a quinoxalyl group.

The substituted or unsubstituted alkenyl group having 1 to 20 carbon atoms represented by any one of $Q^1$ to $Q^{12}$, which is preferably, for example, anyone of (1- and 2-)phenylalkenyl groups, (1,2- and 2,2-)diphenylalkenyl groups, and a (1,2,2-)triphenylalkenyl group each having at least one phenyl group as a substituent, may be unsubstituted.

The alkoxy group and the alkylthio group each represented by any one of $Q^1$ to $Q^{12}$ may each have a substituent, and may each preferably have the above-mentioned alkyl group.

The aryloxy group and the arylthio group each represented by any one of $Q^1$ to $Q^{12}$ may each have a substituent, and each preferably have an aryl group. Specific examples of the aryloxy group include (o-, m-, and p-)phenoxy groups, and specific examples of the arylthio group include (o-, m-, and p-)phenylthio groups.

The aralkyl group represented by any one of $Q^1$ to $Q^{12}$ may have a substituent, and specific examples of the group include a benzyl group and a phenethyl group.

When each of $Q^1$ to $Q^{12}$ have a substituent, particularly in $Q^1$ to $Q^4$, at least two of these substituents are each preferably any one of an aryl group, an amino group, a heterocyclic group, an alkenyl group, and an aryloxy group, or particularly preferably the aryl group. The aryl group, the amino group, the heterocyclic group, and the alkenyl group are each similar to that represented by any one of $Q^1$ to $Q^4$ described above.

Two or more kinds of those substituents may form a fused ring. In addition, each of those substituents may be further substituted, and a preferable substituent in the case is similar to that described above.

When each of $Q^1$ to $Q^{12}$ has a substituent, at least two kinds of, in particular, $Q^1$ to $Q^4$ each preferably have any one of the above substituents. The substitution position of each of the substituents is not particularly limited, and, when $Q^1$ to $Q^4$ each have a phenyl group, the phenyl group may be present at any one of meta, para, and ortho positions.

It is preferable that at least one of $Q^1$ to $Q^6$ in the formula (1) represent a substituted or unsubstituted aryl group, and it is more preferable that at least one of $Q^1$ to $Q^4$ represent a substituted or unsubstituted aryl group.

In particular, the naphthacene derivative is more preferably represented by the formula (2).

In the formula (2), $Q^3$ to $Q^{12}$, $Q^{101}$ to $Q^{105}$, and $Q^{201}$ to $Q^{205}$ each represent hydrogen, a substituted or unsubstituted alkyl group, a substituted or unsubstituted aryl group, a substituted or unsubstituted amino group, a substituted or unsubstituted alkoxy group, a substituted or unsubstituted alkylthio group, a substituted or unsubstituted aryloxy group, a substituted or unsubstituted arylthio group, a substituted or unsubstituted alkenyl group, a substituted or unsubstituted aralkyl group, or a substituted or unsubstituted heterocyclic group, and $Q^3$ to $Q^{12}$, $Q^{101}$ to $Q^{105}$, and $Q^{201}$ to $Q^{205}$ may be identical to or different from one another. Two or more adjacent groups of $Q^{101}$ to $Q^{105}$, and $Q^{201}$ to $Q^{205}$ may be bonded to each other to form a ring.

Specific examples of each of those groups are similar to those of, for example, $Q^1$ in the formula (1).

In the formula (2), $Q^{101}$ to $Q^{105}$ and $Q^{201}$ to $Q^{205}$ each preferably represent any one of hydrogen, an aryl group, an amino group, a heterocyclic group, an aryloxy group, and an alkenyl group, or particularly preferably the aryl group. In addition, at least one of those groups has, as a substituent, preferably any one of an aryl group, an amino group, a heterocyclic group, and an aryloxy group, or particularly preferably the aryl group. Two or more adjacent groups of them may form a fused ring. Preferable examples of each of the aryl group, the amino group, the heterocyclic group, and the aryloxy group are similar to those of any one of $Q^1$ to $Q^{12}$ described above.

In addition, $Q^{101}$ to $Q^{105}$, or $Q^{201}$ to $Q^{205}$, which are preferably identical to one another, may be different from one another. An amino group as a substituent for any one of $Q^{101}$ to $Q^{105}$, and $Q^{201}$ to $Q^{205}$ may be any one of, for example, an alkylamino group, an arylamino group, and an aralkylamino group. The amino group preferably has an aliphatic hydrocarbon group having 1 to 6 carbon atoms in total and/or an aromatic carbon ring which is monocyclic, bicyclic, tricyclic, or tetracyclic. Specific examples of the amino group include a dimethylamino group, a diethylamino group, a butylamino group, a diphenylamino group, a ditolylamino group, a bisdiphenylamino group, and a bisnaphthylamino group.

Examples of the fused ring to be formed include indene, naphthalene, anthracene, phananthrene, quinoline, isoquinoline, quiqunosaline, phenazine, acridine, indole, carbazole, phenoxazine, phenothiazine, benzothiazole, benzothiophene, benzofuran, acridone, banzoimidazole, coumarine, and flavon.

$Q^3$, $Q^4$, and $Q^9$ to $Q^{12}$ each particularly preferably represent hydrogen.

Specific examples of the aromatic compound represented by the general formula (1) of the present invention are shown below. However, the present invention is not limited to these exemplified compounds.

[Chemical formula 4]

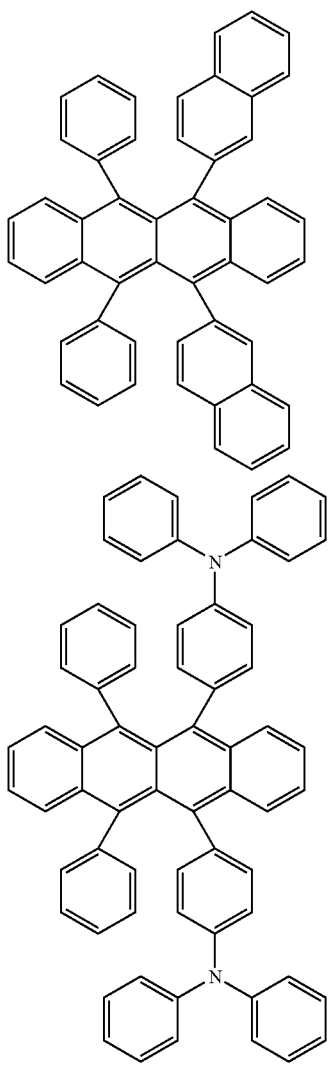

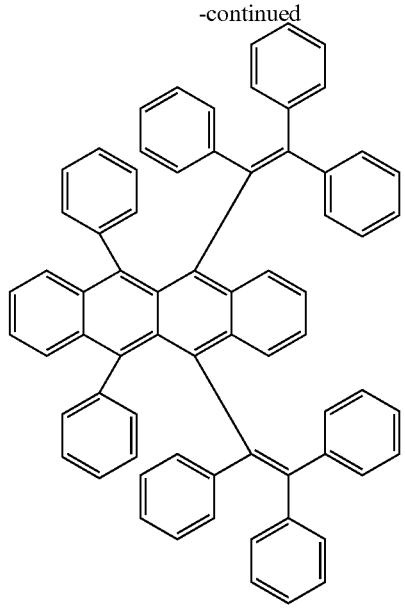

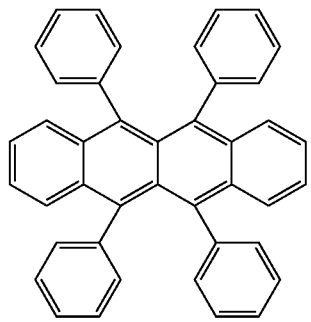

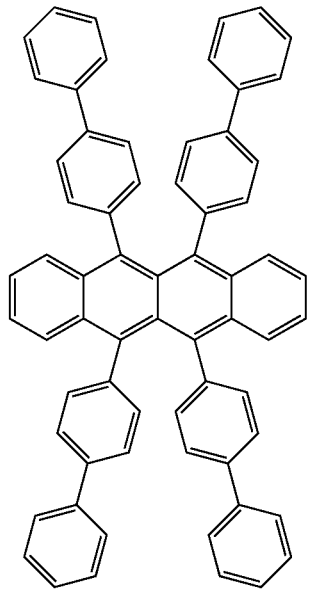

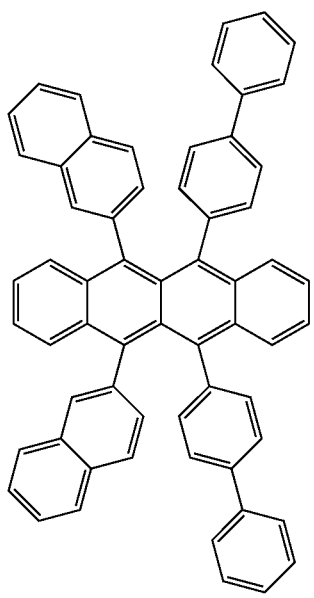
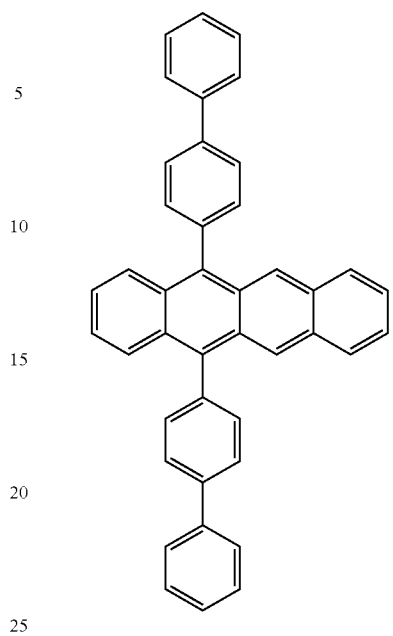
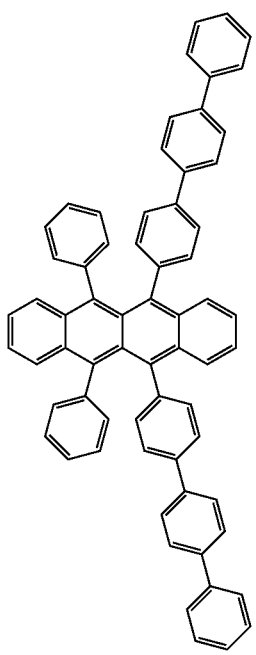

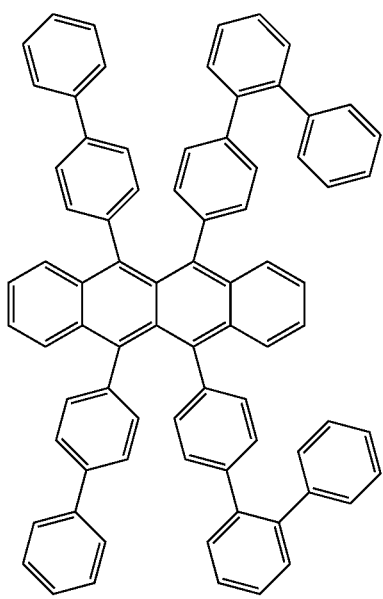
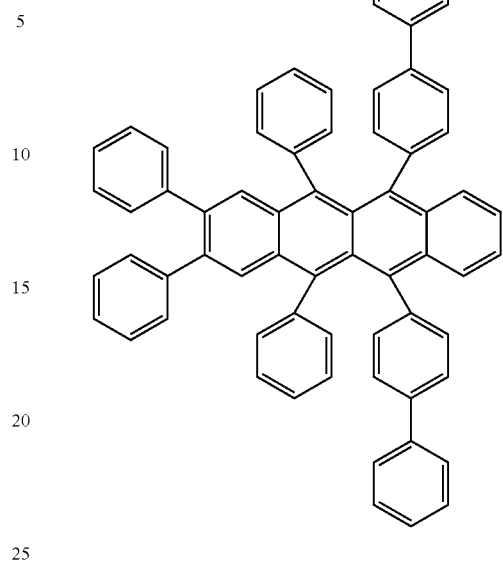
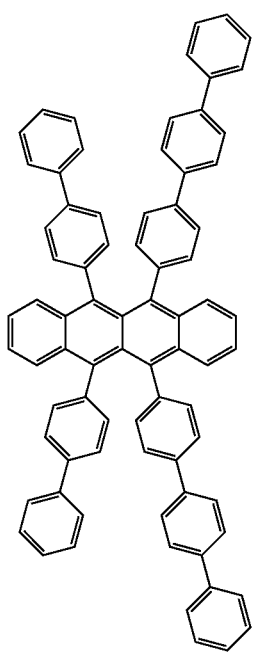
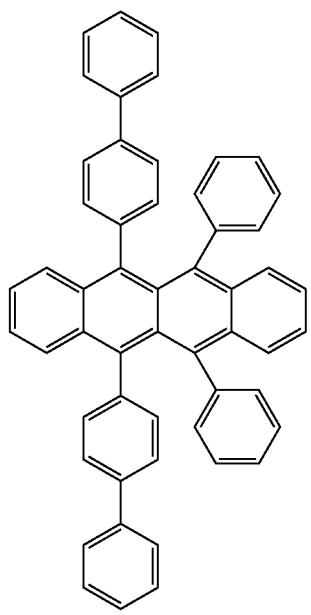

-continued

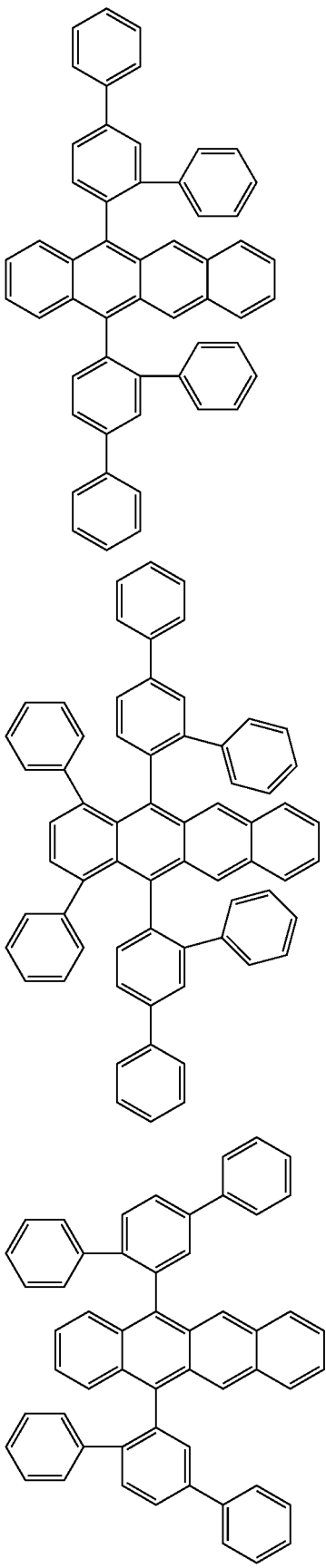

[Hole Transporting Layer and Hole Injecting Layer]

The hole transporting layer is a layer which helps injection of holes into the emitting layer and transports the holes to the light-emitting region. The layer exhibits a great mobility of holes and, in general, has an ionization energy as small as 5.5 eV or smaller. For the hole transporting layer, a material which transports holes to the emitting layer under an electric field of a smaller strength is preferable. A material which exhibits, for example, a mobility of holes of at least $10^{-4}$ cm$^2$/V·sec under application of an electric field of $10^4$ to $10^6$ V/cm is preferable.

The material which can be used for forming the hole transporting layer is not particularly limited as long as the material has the described preferable property. The material can be selected from materials which are conventionally used as the charge transporting material of holes in photoconductive materials and conventional and known materials which are used for the hole transporting layer in organic EL devices, and can be used.

Specific examples include: a triazole derivative (see, for example, U.S. Pat. No. 3,112,197); an oxadiazole derivative (see, for example, U.S. Pat. No. 3,189,447); an imidazole derivative (see, for example, JP 37-16096 B); a polyarylalkane derivative (see, for example, U.S. Pat. No. 3,615,402, U.S. Pat. No. 3,820,989, U.S. Pat. No. 3,542,544, JP 45-555 B, JP 51-10983 B, JP 51-93224 A, JP 55-17105 A, JP 56-4148 A, JP 55-108667 A, JP 55-156953 A, and JP 56-36656 A); a pyrazoline derivative and a pyrazolone derivative (see, for example, U.S. Pat. No. 3,180,729, U.S. Pat. No. 4,278,746, JP 55-88064 A, JP 55-88065 A, JP 49-105537 A, JP 55-51086 A, JP 56-80051 A, JP 56-88141 A, JP 57-45545 A, JP 54-112637A, and JP 55-74546 A); a phenylenediamine derivative (see, for example, U.S. Pat. No. 3,615,404, JP51-10105 B, JP46-3712 B, JP47-25336 B, and JP54-119925 A); an arylamine derivative (see, for example, U.S. Pat. No. 3,567,450, U.S. Pat. No. 3,240,597, U.S. Pat. No. 3,658,520, U.S. Pat. No. 4,232,103, U.S. Pat. No. 4,175,961, U.S. Pat. No. 4,012,376, JP 49-35702 B, JP 39-27577 B, JP 55-144250 A, JP 56-119132 A, JP 56-22437 A, and DE 1,110,518); an amino-substituted chalcone derivative (see, for example, U.S. Pat. No. 3,526,501); an oxazole derivative (those disclosed in U.S. Pat. No. 3,257,203); a styrylanthracene derivative (see, for example, JP 56-46234 A); a fluorenone derivative (see, for example, JP54-110837A); a hydrazone derivative (see, for example, U.S. Pat. No. 3,717,462, JP 54-59143 A, JP 55-52063 A, JP 55-52064 A, JP 55-46760 A, JP 57-11350 A, JP 57-148749 A, and JP 2-311591 A); a stilbene derivative (see, for example, JP 61-210363 A, JP 61-228451 A, JP 61-14642 A, JP 61-72255 A, JP 62-47646 A, JP 62-36674 A, JP 62-10652 A, JP 62-30255 A, JP 60-93445 A, JP 60-94462 A, JP 60-174749 A, and JP 60-175052 A); a silazane derivative (U.S. Pat. No. 4,950,950); a polysilane-based (JP 2-204996 A); an aniline-based copolymer (JP 2-282263A); and an electroconductive high molecular weight oligomer (particularly a thiophene oligomer).

A material represented by the following formula (3) is preferably used.

$$Q^1\text{-G-}Q^2 \qquad (3)$$

In the formula (3), $Q^1$ and $Q^2$ each represent a site having at least one tertiary amine, and G represents a linking group.

An amine derivative represented by the following general formula is more preferably used.

[Chemical formula 5]

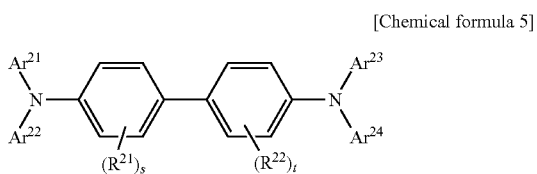

[Chemical formula 6]

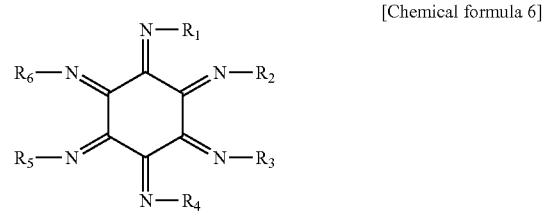

In the above general formula, $Ar^{21}$ to $Ar^{24}$ each represent a substituted or unsubstituted aromatic ring having 6 to 50 carbon atoms forming the aromatic ring, or a substituted or unsubstituted heterocyclic aromatic ring having 5 to 50 atoms forming the ring, $R^{21}$ and $R^{22}$ each represent a substituent, s and t each represent an integer of 0 to 4, $Ar^{21}$ and $Ar^{22}$, or $Ar^{23}$ and $Ar^{24}$ may be linked to each other to form a cyclic structure, and $R^{21}$ and $R^{22}$ may also be linked to each other to form a cyclic structure.

The substituents of $Ar^{21}$ to $Ar^{24}$, and $R^{21}$ and $R^{22}$ are each a substituted or unsubstituted aromatic ring having 6 to 50 carbon atoms forming the aromatic ring, a substituted or unsubstituted heterocyclic aromatic ring having 5 to 50 atoms forming the ring, an alkyl group having 1 to 50 carbon atoms, an alkoxy group having 1 to 50 carbon atoms, an alkylaryl group having 1 to 50 carbon atoms, an aralkyl group having 1 to 50 carbon atoms, a styryl group, an amino group substituted with an aromatic ring having 6 to 50 ring carbon atoms or heterocyclic aromatic ring having 5 to 50 ring atoms, or an aromatic ring which has 6 to 50 ring carbon atoms and which is substituted with an amino group substituted with an aromatic ring having 6 to 50 ring carbon atoms or heterocyclic aromatic ring having 5 to 50 ring atoms or a heterocyclic aromatic ring which has 5 to 50 ring atoms and which is substituted with the amino group.

A hole injecting layer can also be separately provided in addition to a hole transporting layer to help an injection of holes. The same material as that used for the hole transporting layer can be used as the material for the hole injecting layer. A porphyrin compound (those disclosed in, for example, JP 63-295695 A); an aromatic tertiary amine compound and a styrylamine compound (see, for example, U.S. Pat. No. 4,127,412, JP 53-27033 A, JP 54-58445 A, JP 54-149634A, JP54-64299A, JP55-79450A, JP55-144250A, JP56-119132 A, JP61-295558A, JP61-98353A, and JP63-295695A); are preferable, and aromatic tertiary amines are particularly preferable.

Further examples of the material for the hole injecting layer include compounds having two fused aromatic rings in the molecule such as 4,4-bis(N-(1-naphthyl)-N-phenylamino)-biphenyl (hereinafter referred to as NPD) as disclosed in U.S. Pat. No. 5,061,569, and a compound in which three triphenylamine units are bonded together in a star-burst shape, such as 4,4',4''-tris(N-(3-methylphenyl)-N-phenylamino)-triphenylamine (hereinafter referred to as MTDATA) as disclosed in JP 4-308688 A can be exemplified.

In addition to the foregoing, a nitrogen-containing heterocyclic derivative disclosed in Japanese Patent No. 03571977 and represented by the following general formula can also be used.

In the above general formula, $R_1$ to $R_6$ each represent any one of a substituted or unsubstituted alkyl group, a substituted or unsubstituted aryl group, a substituted or unsubstituted aralkyl group, and a substituted or unsubstituted heterocyclic group, provided that $R_1$ to $R_6$ may be identical to or different from one another, and $R_1$ and $R_2$, $R_3$ and $R_4$, $R_5$ and $R_6$, $R_1$ and $R_6$, $R_2$ and $R_3$, or $R_4$ and $R_5$ may form a fused ring. Further, a compound disclosed in US 2004/113547A1 and represented by the following general formula can also be used.

[Chemical formula 7]

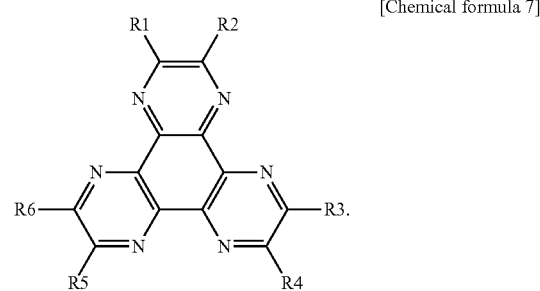

In the above general formula, R1 to R6 each represent a substituent, or preferably an electron-withdrawing group such as a cyano group, a nitro group, a sulfonyl group, a carbonyl group, a trifluoromethyl group, or a halogen.

Further, in addition to the aromatic dimethylidene-based compounds, inorganic compounds such as Si of the p-type and SiC of the p-type can also be used as the material for the hole injecting layer.

The hole injecting layer and the hole transporting layer can be formed by the compound described above in accordance with a conventional method such as the vacuum vapor deposition method, the spin coating method, the casting method, and the LB method. The thicknesses of the hole injecting layer and the hole transporting layer are not particularly limited. In general, the thickness is 5 nm to 5 µm. The hole injecting layer and the hole transporting layer may be constituted with a single layer formed of one or more materials described above, or may be a laminate formed of the hole injecting layer and the hole transporting layer made of materials different from the materials of the hole injecting layer and the hole transporting layer described above as long as the hole injecting layer and the hole transporting layer includes the compound in the hole transporting zone.

Further, an organic semiconductor layer is part of the hole transporting layer, and is a layer helping the injection of holes or electrons into the emitting layer. As the organic semiconductor layer, a layer having a conductivity of $10^{-10}$ S/cm or greater is preferable. As the material for the organic semiconductor layer, oligomers containing thiophene, conductive oligomers such as oligomers containing arylamine, and conductive dendrimers such as dendrimers containing arylamine which are disclosed in JP 08-193191 A, can be used.

[Electron Injecting/Transporting Layer (Electron Transporting Area)]

An electron injecting/transporting layer may be further laminated on the cathode side of the emitting medium layer. The electron injecting layer is a layer which helps injection of electrons into the emitting medium layer and exhibits a great mobility of electrons. The electron transporting layer can be suitably selected from the layers having a film thickness of several nm to several μm. When the film is thick, a mobility of electrons of a least $10^{-5}$ cm$^2$/Vs under application of an electric field of $10^4$ to $10^6$ V/cm is desirable so that voltage increase can be avoided.

As the material used for the electron injecting layer, metal complexes of 8-hydroxyquinoline and derivatives thereof or a nitrogen-containing heterocyclic compound are preferable.

Examples of the above-mentioned metal complexes of 8-hydroxyquinoline or its derivatives include metal chelate oxinoide compounds containing the chelate of oxine (in general, 8-quinolinol or 8-hydroxyquinoline). For example, Alq having Al as a main metal may be used as an electron injecting layer.

On the other hand, examples of the oxadiazole derivative include electron transfer compounds represented by the following general formulae.

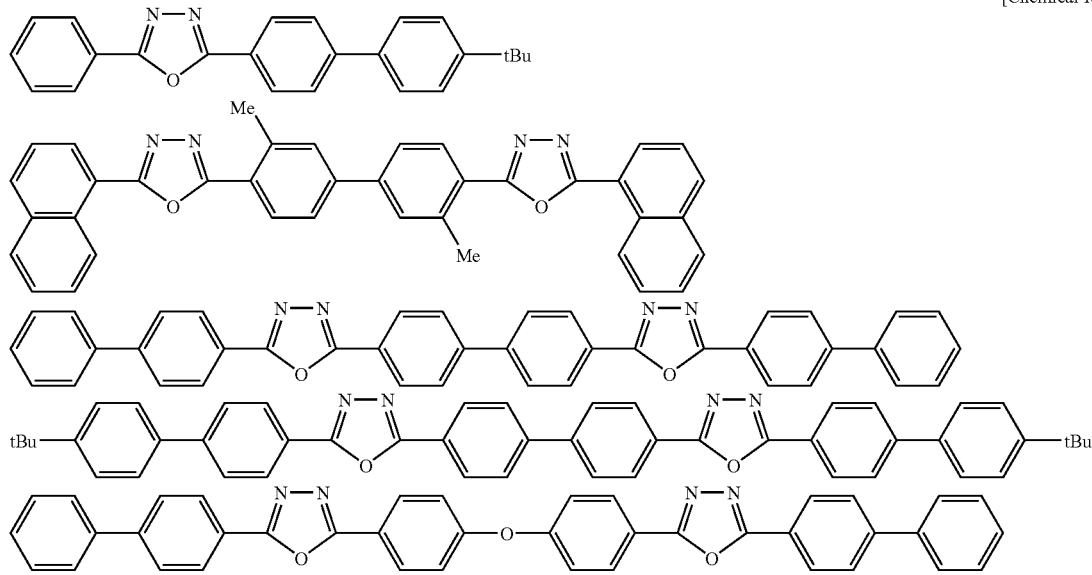

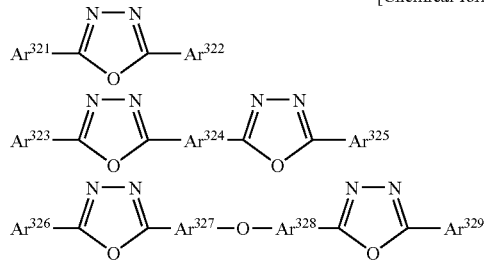

[Chemical formula 8]

In the formulae, $Ar^{321}$, $Ar^{322}$, $Ar^{323}$, $Ar^{325}$, $Ar^{326}$ and $Ar^{329}$ each represent a substituted or unsubstituted aryl group and may represent the same group or different groups. $Ar^{324}$, $Ar^{327}$ and $Ar^{328}$ each represent a substituted or unsubstituted arylene group and may represent the same group or different groups.

Examples of the aryl group include a phenyl group, a biphenyl group, an anthranyl group, a perylenyl group, and a pyrenyl group. Examples of the arylene group include a phenylene group, a naphthylene group, a biphenylene group, an anthranylene group, a perylenylene group, and a pyrenylene group. Examples of the substituent include alkyl groups having 1 to 10 carbon atoms, alkoxyl groups having 1 to 10 carbon atoms, or a cyano group. As the electron transfer compound, compounds which can form thin films are preferable.

Examples of the electron transfer compounds described above include compounds represented by the following formulae.

[Chemical formula 9]

Me represents a methyl group, and Bu represents a butyl group.

Nitrogen-containing heterocyclic derivatives represented by the following general formulae

[Chemical formula 10]

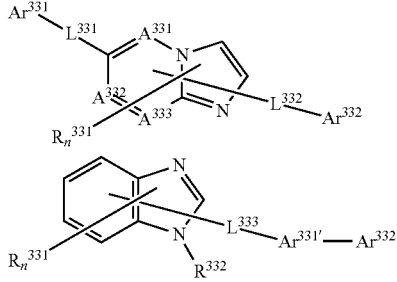

In the above respective general formulae:

$A^{331}$ to $A^{333}$ each represent a nitrogen atom or a carbon atom;

$R^{331}$ and $R^{332}$ each represent a substituted or unsubstituted aryl group having 6 to 60 carbon atoms, a substituted or unsubstituted heteroaryl group having 3 to 60 carbon atoms, an alkyl group having 1 to 20 carbon atoms, a haloalkyl group having 1 to 20 carbon atoms, or an alkoxy group having 1 to 20 carbon atoms, n represents an integer of 0 to 5, and, when n represents an integer of 2 or more, multiple $R^{331}$'s may be identical to or different from each other, or multiple adjacent $R^{331}$ groups may be bonded to each other to form a substituted or unsubstituted carbocyclic aliphatic ring, or a substituted or unsubstituted carbocyclic aromatic ring;

$Ar^{331}$ represents a substituted or unsubstituted aryl group having 6 to 60 carbon atoms, or a substituted or unsubstituted heteroaryl group having 3 to 60 carbon atoms;

$Ar^{331}$ represents a substituted or unsubstituted arylene group having 6 to 60 carbon atoms, or a substituted or unsubstituted heteroarylene group having 3 to 60 carbon atoms;

$Ar^{332}$ represents a hydrogen atom, an alkyl group having 1 to 20 carbon atoms, a haloalkyl group having 1 to 20 carbon atoms, an alkoxy group having 1 to 20 carbon atoms, a substituted or unsubstituted aryl group having 6 to 60 carbon atoms, or a substituted or unsubstituted heteroaryl group having 3 to 60 carbon atoms, provided that one of $Ar^{331}$ and $Ar^{332}$ represents a substituted or unsubstituted fused ring group having 10 to 60 carbon atoms, or a substituted or unsubstituted heterofused ring group having 3 to 60 carbon atoms; and $L^{331}$, $L^{332}$, and $L^{333}$ each represent a single bond, a substituted or unsubstituted fused ring having 6 to 60 carbon atoms, a substituted or unsubstituted heterofused ring having 3 to 60 carbon atoms, or a substituted or unsubstituted fluorenylene group.

A nitrogen-containing heterocyclic derivative described in Japanese Patent Application Laid-Open No. 2004-002297 and represented by the following formula

In the above formula, HAr represents a substituted or unsubstituted nitrogen-containing heterocycle having 3 to 40 carbon atoms, $L^{341}$ represents a single bond, a substituted or unsubstituted arylene group having 6 to 60 carbon atoms, a substituted or unsubstituted heteroarylene group having 3 to 60 carbon atoms, or a substituted or unsubstituted fluorenylene group, $Ar^{341}$ represents a substituted or unsubstituted, divalent aromatic hydrocarbon group having 6 to 60 carbon atoms, and $Ar^{342}$ represents a substituted or unsubstituted aryl group having 6 to 60 carbon atoms, or a substituted or unsubstituted heteroaryl group having 3 to 60 carbon atoms.

A silacyclopentadiene derivative described in Japanese Patent Application Laid-Open No. Hei 09-087616 and represented by the following general formula

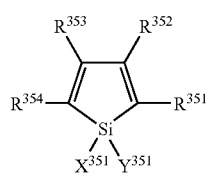

[Chemical formula 11]

In the above formula, $X^{351}$ and $Y^{351}$ each independently represent a saturated or unsaturated hydrocarbon, alkoxy, alkenyloxy, or alkynyloxy group having 1 to 6 carbon atoms, a substituted or unsubstituted aryl group, or a substituted or unsubstituted heterocycle, or $X^{351}$ and $Y^{351}$ are bonded to each other to form a saturated or unsaturated ring, $R^{351}$ to $R^{354}$ each independently represent hydrogen, a halogen, a saturated or unsaturated alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or, when substituted or unsubstituted rings are adjacent to each other, the rings fuse with each other.

A silacyclopentadiene derivative described in JP 09-194487 A and represented by the following general formula

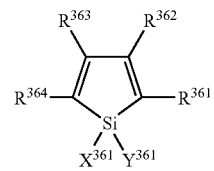

[Chemical formula 12]

In the above formula, $X^{361}$ and $Y^{361}$ each independently represent a saturated or unsaturated hydrocarbon, alkoxy, alkenyloxy, or alkynyloxy group having 1 to 6 carbon atoms, a substituted or unsubstituted aryl group, or a substituted or unsubstituted heterocycle, or $X^{361}$ and $Y^{361}$ are bonded to each other to form a saturated or unsaturated ring, $R^{361}$ to $R^{364}$ each independently represent hydrogen, a halogen, a saturated or unsaturated alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or, when substituted or unsubstituted rings represented by two arbitrary symbols of $R^{361}$ to $R^{364}$ are adjacent to each other, the rings fuse with each other (provided that, when $R^{361}$ and $R^{364}$ each represent a phenyl group, none of $X^{361}$ and $Y^{361}$ represents an alkyl group or a phenyl group, when $R^{361}$ and $R^{364}$ each represent a thienyl group, a state where $X^{361}$ and $Y^{361}$ each represent a monovalent hydrocarbon group and a state where $R^{362}$ and $R^{363}$ each represent an alkyl group, an aryl group, or an alkenyl group, or $R^{362}$ and $R^{363}$ represent aliphatic groups to be bonded to each other to form a ring are not simultaneously satisfied, when $R^{361}$ and $R^{364}$ each represent a silyl group, $R^{362}$, $R^{363}$, $X^{361}$, and $Y^{361}$ each independently represent a group except a monovalent hydrocarbon group having 1 to 6 carbon atoms and a hydrogen atom, and, when benzene rings fuse with each other at $R^{361}$ and $R^{362}$, none of $X^{361}$ and $Y^{361}$ represents an alkyl group or a phenyl group.

A borane derivative described in JP 2000-040586 A and represented by the following general formula

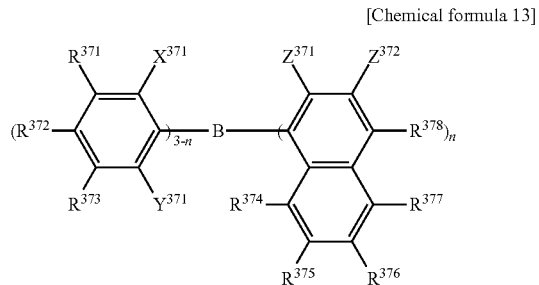

[Chemical formula 13]

In the above general formula, $R^{371}$ to $R^{378}$ and $Z^{372}$ each independently represent a hydrogen atom, a saturated or unsaturated hydrocarbon group, an aromatic group, a heterocyclic group, a substituted amino group, a substituted boryl group, an alkoxy group, or an aryloxy group, $X^{371}$, $Y^{371}$, and $Z^{371}$ each independently represent a saturated or unsaturated hydrocarbon group, an aromatic group, a heterocyclic group, a substituted amino group, an alkoxy group, or an aryloxy group, the substituents of $Z^{371}$ and $Z^{372}$ may be bonded to each other to form a fused ring, n represents an integer of 1 to 3, and, when n represents 2 or more, $Z^{371}$'s may be different from each other, provided that the case where n represents 1, $X^{371}$, $Y^{371}$, and $R^{372}$ each represent a methyl group, and $R^{378}$ represents a hydrogen atom or a substituted boryl group, and the case where n represents 3 and $Z^{371}$ represents a methyl group are excluded.

A compound described in JP 10-088121 A and represented by the following general formula

[Chemical formula 14]

In the above general formula, $Q^{381}$ and $Q^{382}$ each independently represent a ligand represented by the following formula, $L^{381}$ represents a halogen atom, a substituted or unsubstituted alkyl group, a substituted or unsubstituted cycloalkyl group, a substituted or unsubstituted aryl group, a substituted or unsubstituted heterocyclic group, or a ligand represented by —$OR^{391}$ ($R^{391}$ represents a hydrogen atom, a substituted or unsubstituted alkyl group, a substituted or unsubstituted cycloalkyl group, a substituted or unsubstituted aryl group, or a substituted or unsubstituted heterocyclic group) or by —O—Ga-$Q^{391}(Q^{392})$ ($Q^{391}$ and $Q^{392}$ each have the same meaning as that of each of $Q^{381}$ and $Q^{382}$)

[Chemical formula 15]

In the above formula, rings $A^{401}$ and $A^{402}$ are substituted or unsubstituted aryl ring structures or heterocyclic structures bonded to each other.

Specific examples of the substituent of the rings $A^{401}$ and $A^{402}$ each forming the ligand in the above formula include: halogen atoms such as chlorine, bromine, iodine, and fluorine; substituted or unsubstituted alkyl groups such as a methyl group, an ethyl group, a propyl group, a butyl group, a sec-butyl group, a tert-butyl group, a pentyl group, a hexyl group, a heptyl group, an octyl group, a stearyl group, and a trichloromethyl group; substituted or unsubstituted aryl groups such as a phenyl group, a naphthyl group, a 3-methylphenyl group, a 3-methoxyphenyl group, a 3-fluorophenyl group, a 3-trichloromethylphenyl group, a 3-trifluoromethylphenyl group, and a 3-nitrophenyl group; substituted and unsubstituted alkoxy groups such as a methoxy group, an n-butoxy group, a tert-butoxy group, a trichloromethoxy group, a trifluoroethoxy group, a pentafluoropropoxy group, a 2,2,3,3-tetrafluoropropoxy group, a 1,1,1,3,3,3-hexafluoro-2-propoxy group, and a 6-(perfluoroethyl)hexyloxy group; substituted or unsubstituted aryloxy groups such as a phenoxy group, a p-nitrophenoxy group, a p-tert-butylphenoxy group, a 3-fluorophenoxy group, a pentafluorophenyl group, and a 3-trifluoromethylphenoxy group; substituted or unsubstituted alkylthio groups such as a methylthio group, an ethylthio group, a tert-butylthio group, a hexylthio group, an octylthio group, and a trifluoromethylthio group; substituted or unsubstituted arylthio groups such as a phenylthio group, a p-nitrophenylthio group, a ptert-butylphenylthio group, a 3-fluorophenylthio group, a pentafluorophenylthio group, and a 3-trifluoromethylphenylthio group; mono- or di-substituted amino groups such as a cyano group, a nitro group, an amino group, a methylamino group, a diethylamino group, an ethylamino group, a diethylamino group, a dipropylamino group, a dibutylamino group, and a diphenylamino group; acylamino groups such as bis(acetoxymethyl)amino group, bis(acetoxyethyl)amino group, bisacetoxypropyl)amino group, and bis(acetoxybutyl)amino group; a hydroxy group; a siloxy group; an acyl group; carbamoyl groups such as a methylcarbamoyl group, a dimethylcarbomoyl group, an ethylcarbamoyl group, a diethylcarbamoyl group, a propylcarbamoyl group, a butylcarbamoyl group, and a phenylcarbamoyl group; a carboxyl group; a sulfone group; an imide group; cycloalkyl groups such as a cyclopentane group and a cyclohexyl group; aryl groups such as a phenyl group, a naphthyl group, a biphenyl group, an anthranyl group, a phenanthryl group, a fluorenyl group, and a pyrenyl group; heterocyclic groups such as a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a carbazolyl group, a furanyl group, a thiophenyl group, an oxazolyl group, an oxadiazolyl group, a benzooxazolyl group, a thiazolyl group, a thiadiazolyl group, a benzothiazolyl group, a triazolyl group, an imidazolyl group, and a benzoimidazolyl group. In addition, the above-mentioned substituents may bind to each other to form a 6-membered aryl ring or a heterocyclic ring.

A preferable embodiment of the present invention includes a device including a reducing dopant in the region of electron transport or in the interfacial region of the cathode and the organic layer. The reducing dopant is defined as a substance which can reduce a compound having the electron transporting property. Various compounds can be used as the reducing dopant as long as the compounds have a uniform reductive property. For example, at least one substance selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, organic complexes of alkali metals, organic complexes of alkaline earth metals, and organic complexes of rare earth metals can be suitably used.

More specifically, examples of the preferable reducing dopant includes substances having a work function of 2.9 eV or smaller, specific examples of which include at least one alkali metal selected from the group consisting of Na (the work function: 2.36 eV), K (the work function: 2.28 eV), Rb (the work function: 2.16 eV), and Cs (the work function: 1.95 eV), and at least one alkaline earth metal selected from the group consisting of Ca (the work function: 2.9 eV), Sr (the work function: 2.0 to 2.5 eV), and Ba (the work function: 2.52 eV). Among the above substances, at least one alkali metal selected from the group consisting of K, Rb and Cs is more preferable, Rb, and Cs are still more preferable, and Cs is most preferable as the reducing dopant. These alkali metals have great reducing ability, and the luminance of the emitted light and the life of the organic EL device can be increased by addition of a relatively small amount of the alkali metal into the electron injecting zone. In addition, as the reducing dopant having a work function of 2.9 eV or smaller, combinations of two or more alkali metals thereof are also preferable. Combinations having Cs such as the combinations of Cs and Na, Cs and K, Cs and Rb, and Cs, Na, and K are more preferable. The reducing ability can be efficiently exhibited by the combination having Cs. The luminance of emitted light and the life of the organic EL device can be increased by adding the combination having Cs into the electron injecting zone.

The present invention may further include an electron injecting layer which is constituted with an insulating material or a semiconductor and disposed between the cathode and the organic layer. At this time, leak of electric current can be effectively prevented by the electron injecting layer, and the electron injecting property can be improved. As the insulating material, at least one metal compound selected from the group consisting of alkali metal chalcogenides, alkaline earth metal chalcogenides, alkali metal halides, and alkaline earth metal halides is preferable. It is preferable that the electron injecting layer be constituted with the above substance such as the alkali metal chalcogenide since the electron injecting property can be further improved. Preferable examples of the alkali metal chalcogenide include $Li_2O$, LiO, $Na_2S$, $Na_2Se$, and NaO. Preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluoride such as $CaF_2$, $BaF_2$, $SrF_2$, $MgF_2$, and $BeF_2$ and halides other than the fluorides.

Examples of the semiconductor constituting the electron transporting layer include oxides, nitrides, and oxide nitrides of at least one element selected from Ba, Ca, Sr, Yb, Al, Ga, In, Li, Na, Cd, Mg, Si, Ta, Sb, and Zn used singly or in combination of two or more. In addition, it is preferable that the inorganic compound constituting the electron transporting layer form a crystallite or amorphous insulating thin film. When the electron injecting layer is constituted with the insulating thin film described above, a more uniform thin film can be formed, and defects of pixels such as dark spots can be decreased. It should be noted that examples of the inorganic compound include alkali metal chalcogenides, alkaline earth metal chalcogenides, alkali metal halides, and alkaline earth metal halides which are described above.

[Cathode]

As the cathode, a material such as a metal, an alloy, a conductive compound, or a mixture of these materials, which have a small work function (4 eV or smaller), is used as the electrode material. Examples of the electrode material include sodium, sodium-potassium alloys, magnesium, lithium, magnesium-silver alloys, aluminum/aluminum oxide, aluminum-lithium alloys, indium, and rare earth metals.

The cathode can be prepared by forming a thin film of the electrode material described above in accordance with a method such as the vapor deposition method and the sputtering method.

In the case of a top surface emission type on top emission type organic EL device, it is preferable that the transmittance of the cathode be greater than 10% with respect to emission from the emitting layer.

It is also preferable that the sheet resistivity of the cathode be several hundred $\Omega/\square$ or smaller. The thickness of the cathode is, in general, selected in the range of 10 nm to 1 μm and preferably in the range of 50 to 200 nm.

[Insulating Layer]

Defects in pixels tend to be formed in organic EL device due to leak and short circuit since an electric field is applied to ultra-thin films. To prevent the formation of the defects, a layer of a thin film having an insulating property may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide. Mixtures and laminates of the above compounds can also be used.

The present invention provides a coating film-forming ink for forming each organic thin film layer in an organic electroluminescence device composed of the organic compound material and an organic solvent such as an emitting layer, and a method of forming a thin film as well.

The coating film-forming ink of the present invention is composed of an organic solvent solution dispersion containing the organic compound material.

Examples of the organic solvent used for solving the organic compound material of the present invention include halogen-based hydrocarbon solvents such as dichloromethane, dichloroethane, chloroform, carbon tetrachloride, tetrachloroethane, and trichloroethane; ether-based solvents such as dibutyl ether, tetrahydrofuran, and dioxane; alcohol-based solvents such as methanol, ethanol, propanol, butanol, pentanol, hexanol, octanol, nonanol, cyclohexanol, methylcellsolve, ethylcellosolve, ethylene glycol, and benzylalcohol; aromatic solvents which may have an alkyl group, an alkoxy group, or a halogen, such as benzene, toluene, xylene, ethylbenzene, diethylbenzene, tetraline, butylbenzene, dodecylbenzene, anisole, chlorobenzene, dichlorobenzene, and chlorotoluene, hydrocarbon solvents such as hexane, octane, and decane, ester-based solvents such as ethyl acetate, butyl acetate, and amyl acetate, ketone-based solvents such as methylbutyl ketone, cyclohexanone, cycloheptanone, cyclopentanone, and cyclooctanone, an amide-based solvent such as dimethylformamide, and dimethylsulfoxide. Of those, a halogen-based hydrocarbon-based solvent, a hydrocarbon-based solvent, an aromatic solvent, an ether-based solvent, a ketone-based solvent, or an amide-based solvent is preferable. In addition, each of those solvents may be used alone, or multiple kinds of them may be used as a mixture. It should be noted that a usable solvent is not limited to the foregoing.

Each organic thin film layer in an organic EL device such as an emitting layer can be easily formed of the coating film-forming ink of the present invention by any one of various wet methods such as spin coating, dipping, casting, roll coat, flow coating, and ink-jet.

An appropriate binder resin or any one of various appropriate additives may be used in the coating film-forming ink of the present invention as required for the purpose of, for example, improving the property with which a film is formed of the ink or preventing a pinhole in a film formed of the ink.

Examples of the binder resin include a polyvinylcarbazole resin, a polycarbonate resin, a polyester resin, a polyarylate resin, a butyral resin, a polystyrene resin, a polyvinylacetal resin, diallylphthalate resin, an acryl resin, a methacryl resin, a phenol resin, an epoxy resin, a silicone resin, a polysulfone resin, a urea resin, a polyamide resin, a polyurethane resin, a polysulfone resin, a polymethyl(meth)acrylate resin, an insulation resin such as cellulose and copolymers thereof, photoconductivity resins such as poly-N-vinylcarbazole and polysilane, and electrical conductivity resins such as polythiophene and polypyrrole. One kind of the resins may be used alone, or two or more kinds of the resins may be used as a copolymer by mixing.

The ink preferably contains a component that cures by a treatment such as a heat treatment or irradiation with light to immobilize the organic compound material, that is, a component such as a crosslinkable monomer or polymer together with the above binder resin. In particular, when heat resistance in a subsequent step is taken into consideration, a curable resin composition is preferably used. To be specific, a base material resin is, for example, an acrylic resin or silicon resin having a functional group such as a hydroxyl group, a carboxyl group, an alkoxy group, or an amide group. Further, a crosslinking agent or photoinitiator for curing any such crosslinkable polymer component by irradiation with light or a heat treatment can be used. To be specific, a melamine derivative such as methylolated melamine can be used as the crosslinking agent, and a dichromate, a bisazide compound, a radical-based initiator, a cationic initiator, an anionic initiator, or the like can be used as the photoinitiator. In addition, multiple kinds of those photoinitiators can be used as a mixture, or a combination of any one of them and any other sensitizer can be used.

In addition, examples of the various additives include an antioxidant, a UV absorber, and a plasticizer.

The coating film-forming ink of the present invention is preferably a solution having a concentration of about 0.1 to 15% by mass, or additionally specifically about 0.3 to 10% by mass, though the preferable concentration varies depending on the structure and molecular weight of the organic compound material. The organic compound material is preferably used so as to account for 50% by mass or more of the components except the solvent.

[Production Examples of the Organic EL Device]

To prepare the organic EL device, for example, the anode, the emitting layer, and, where necessary, the hole injecting layer, the hole transporting layer, the electron injecting layer, and the electron transporting layer are formed in accordance with the illustrated method using the illustrated materials, and the cathode is formed in the last step. The organic EL device may also be prepared by forming the above layers in the order reverse to that described above, i.e., the cathode being formed in the first step and the anode in the last step.

Hereinafter, production examples of an organic EL device having a construction in which an anode, a hole transporting layer, an emitting layer, an electron transporting layer and a cathode are disposed successively on a light-transmissive substrate will be described.

On a suitable light-transmissive substrate, a thin film made of a material for the anode is formed in accordance with the vapor deposition method or the sputtering method so that the thickness of the formed thin film is 1 μm or smaller and preferably in the range of 10 to 200 nm. The formed thin film is used as the anode. Then, a hole transporting layer is formed on the anode. The hole transporting layer can be formed in accordance with the vacuum vapor deposition method, the spin coating method, the casting method, or the LB method, as described above. The vacuum vapor deposition method is preferable since a uniform film can be easily obtained, and the possibility of formation of pin holes is small. When the hole transporting layer is formed in accordance with the vacuum vapor deposition method, in general, it is preferable that the conditions be suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C. and the thickness of the film: 5 nm to 5 μm; although the conditions of the vacuum vapor deposition are different depending on the used compound (the material for the hole transporting layer) and the crystal structure and the recombination structure of the hole transporting layer to be formed.

Then, the emitting layer is formed on the hole transporting layer formed above. Using a desired organic light-emitting material, a thin film of the organic light-emitting material can be formed in accordance with the vacuum vapor deposition method, the sputtering method, the spin coating method, or the casting method, and the formed thin film is used as the emitting layer. The vacuum vapor deposition method is preferable since a uniform film can be easily obtained, and the possibility of formation of pin holes is small. When the emitting layer is formed in accordance with the vacuum vapor deposition method, in general, the conditions of the vacuum vapor deposition method can be selected in the same ranges as those described for the vacuum vapor deposition of the hole transporting layer although the conditions are different depending on the used compound.

Subsequently, an electron transporting layer is formed on the emitting layer formed above. Similarly to the hole transporting layer and the emitting layer, it is preferable that the electron transporting layer be formed in accordance with the vacuum vapor deposition method since a uniform film must be obtained. The conditions of the vacuum vapor deposition can be selected in the same ranges as those described for the vacuum vapor deposition of the hole transporting layer and the emitting layer.

A cathode is laminated in the last step.

The cathode is made of a metal and can be formed in accordance with the vacuum vapor deposition method or the sputtering method. It is preferable that the vacuum vapor deposition method be used in order to prevent formation of damages on the lower organic layers during the formation of the film. In the above preparation of the organic EL device, it is preferable that the above layers from the anode to the cathode are formed successively while the preparation system is kept in a vacuum after being evacuated once.

It is to be noted that the method of forming the layers in the organic EL device of the present invention is not particularly limited. A conventional method such as a vacuum vapor deposition method, a molecular beam epitaxy method, a spin coating method, a dipping method, a casting method, a bar coating method, and a roll coating method can be used.

The thickness of each layer in the organic thin film layer in the organic EL device of the present invention is not particularly limited. In general, an excessively thin layer tends to have defects such as pin holes, and an excessively thick layer requires a high applied voltage to decrease the efficiency. Therefore, a thickness in the range of several nanometers to 1 μm is preferable. The organic EL device emits light when a direct voltage of 3 to 40V is applied in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

EXAMPLES

Hereinafter, the present invention will be described in detail on the basis of examples. However, the present invention is not limited to the following examples within the gist of the present invention.

Synthesis Example 1

A naphthacene derivative was synthesized via the following route.

[Chemical formula 16]

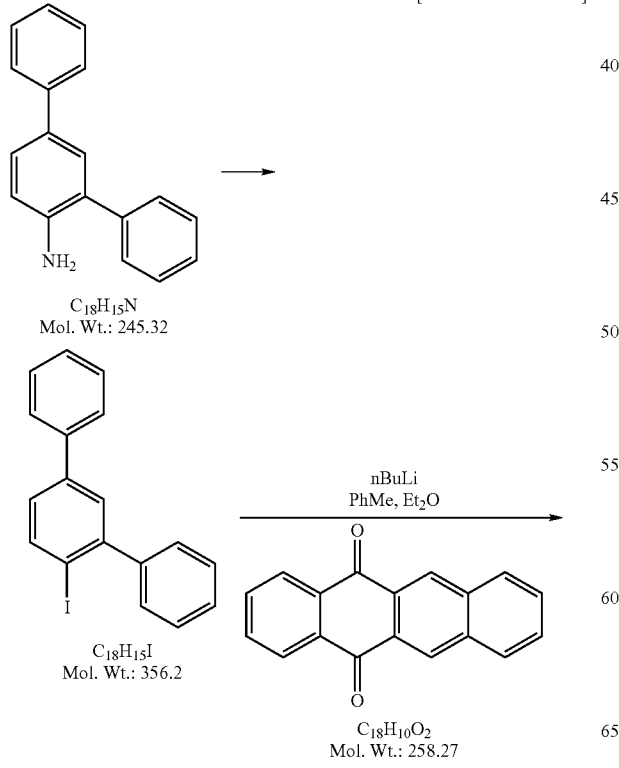

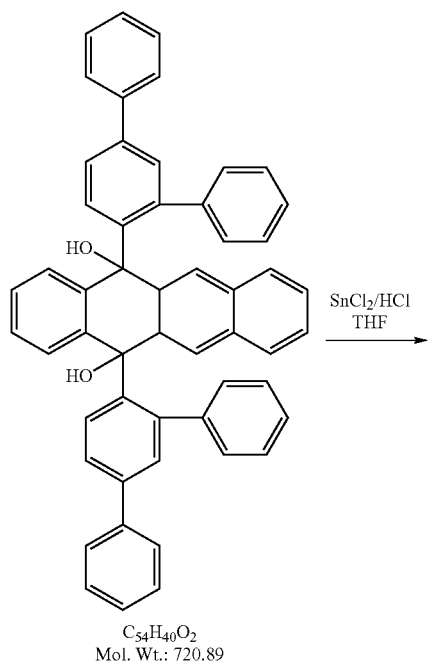

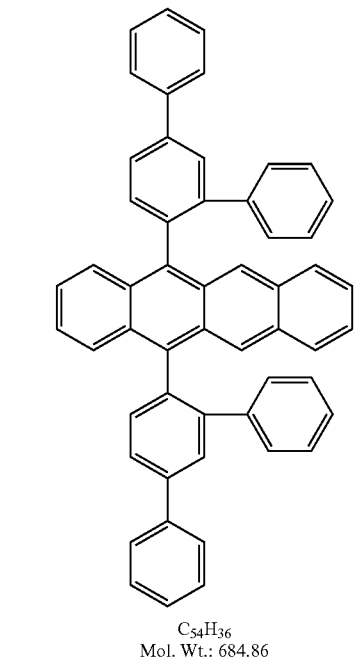 [SMILES: c1ccc(-c2ccc(-c3c4ccccc4c(-c4ccc(-c5ccccc5)cc4-c4ccccc4)c4cc5ccccc5cc34)c(-c3ccccc3)c2)cc1]

Under an argon atmosphere, 300 milliliters of a 3-mol/L aqueous solution of hydrochloric acid were added to 24.5 g of 2,4-diphenylaniline represented by the following formula (4).

[Chemical formula 17]

(4)

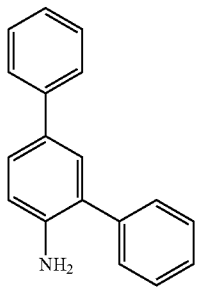

The mixture was heated to 60° C. in an oil bath, and was stirred for 4 hours, whereby a hydrochloride of 2,4-diphenylaniline was obtained in the form of a white suspension. The white suspension was cooled to 5° C. or lower in a salt-ice bath, and a solution prepared by dissolving 8.27 g of sodium nitrite in 60 milliliters of water was dropped to the suspension over 30 minutes while the suspension was stirred. At that time, attention was paid so that the temperature of the resultant liquid might not exceed 10° C. The resultant reddish brown solution was stirred at 5° C. for an additional 1 hour, whereby a diazonium salt solution was prepared.

A solution was prepared by dissolving 60 g of potassium iodide in 180 milliliters of water in a beaker. The above diazonium salt solution was gradually added to the beaker over 30 minutes while the solution in the beaker was stirred. The mixture was stirred for an additional 30 minutes until the generation of a nitrogen gas stopped. After that, 200 milliliters of methylene chloride were added to dissolve the product.

Iodine as a by-product was decomposed by adding a small amount of sodium hydrogen sulfite. After that, an organic layer was separated, washed with an aqueous solution of sodium carbonate and water sequentially, and dried with magnesium sulfate. Methylene chloride and the like were removed by distillation under reduced pressure, and the remainder was purified by column chromatography, whereby 29.4 g of 2,4-diphenyliodobenzene represented by the following formula (5) was obtained (yield: 82.5% by mol).

[Chemical formula 18]

(5)

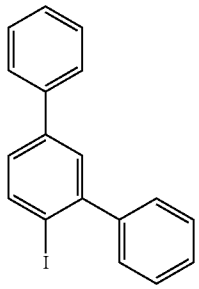

Subsequently, under an argon atmosphere, 27.4 g of 2,4-diphenyliodobenzene were dissolved in 180 milliliters of dehydrated toluene and 60 milliliters of dehydrated ether, and the solution was cooled to −45° C. in a dry ice-acetone bath. 31 milliliters of a 2.44-mol/L solution of n-butyllithium in n-hexane were dropped to the solution over 15 minutes. The temperature of the mixture was slowly increased to −10° C., and the mixture was stirred for an additional 1 hour.

7.75 g of 5,12-naphthacenequinone represented by the following formula (6) were gradually added to the mixture over 30 minutes.

[Chemical formula 19]

(6)

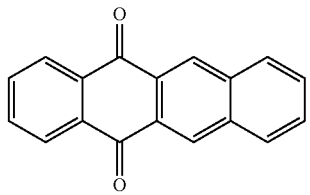

After that, the temperature of the mixture was gradually increased to room temperature, and the mixture was stirred for an additional 5 hours.

The mixture was cooled to 0° C. with ice water, and 60 milliliters of methanol were dropped to the mixture. The resultant powder was taken by filtration, washed with cold methanol several times, and dried in a vacuum, whereby a white powder was obtained. 200 milliliters of toluene were added to the powder so that the powder was suspended and washed under heat for 1 hour, and the mixture was cooled to room temperature. The mixture was filtrated, washed with cold toluene, and dried in a vacuum, whereby 15.1 g of a white powder of a diol compound (hydroxyl group-containing compound) were obtained (yield: 69.8% by mol). 0.6 g of the resultant white powder of the diol compound was taken out and represented by B-3.

The following reaction was performed while a flask provided with an argon-blowing pipe was shield from light with aluminum foil. 450 milliliters of dehydrated tetrahydrofuran (THF) were added to 14.42 g of the diol compound (hydroxyl group-containing compound). The mixture was stirred at room temperature while argon was blown into the mixture, whereby the diol compound was dissolved. After that, the solution was heated to 4° C. in an oil bath. A solution prepared by dissolving 45.1 g of tin dichloride dihydrate in 150 milliliters of concentrated hydrochloric acid was dropped to the above solution over 90 minutes. After that, the temperature of the oil bath was increased to 70° C., and the mixture was stirred under reflux for an additional 2 hours and cooled to room temperature, whereby a reaction liquid was obtained.

A 2-L beaker was shielded from light with aluminum foil, 1 L of distilled water was charged into the beaker, and the beaker was deaerated by flowing an argon stream. The reaction liquid was added to the beaker, and the mixture was stirred for 30 minutes. The precipitated yellow powder was separated by filtration, and was loaded into 1 L of distilled water again, stirred, and washed. The powder was separated by filtration again, sufficiently washed with methanol, and dried in a vacuum. The powder was washed in a state of being suspended in 250 milliliters of acetone deaerated by blowing argon while being refluxed under heat at 70° C., and was separated by filtration. The solid phase separated by filtration was dried in a vacuum, whereby 12.70 g of an orange yellow powder of the target naphthacene derivative were obtained (yield: 92.7% by mol).

The compound was represented by A-1.

A compound obtained by subjecting the compound A-1 to sublimation purification at 320 to 340° C. and $5 \times 10^{-4}$ Pa was represented by A-2.

Subsequently, a compound obtained by subjecting the compound A-2 to sublimation purification at 320 to 340° C.

and $5\times10^{-4}$ Pa again was represented by A-3. The concentration of the diol compound in the compound A-3 was equal to or lower than a detection limit.

The concentration of the diol compound in each of the compounds was analyzed with a high performance liquid chromatograph (HPLC)

Example 1

Test of Organic EL Device for Lifetime

A transparent electrode having a thickness of 130 nm and composed of an indium tin oxide was provided on a glass substrate measuring 25 mm by 75 mm by 0.7 mm. The glass substrate was subjected to ultrasonic cleaning in isopropyl alcohol for 5 minutes. After that, the substrate was subjected to UV-ozone cleaning for 30 minutes, and was placed in a vacuum deposition apparatus.

First of all, N'-bis[4-(N,N-diphenylamino) phenyl-1-yl]-N,N'-diphenyl-4,4'-benzidine was deposited from the vapor onto the substrate so as to serve as a hole injecting layer having a thickness of 60 nm. After that, N,N'-bis[4'-{N-(naphthyl-1-yl)-N-phenyl}aminobiphenyl-4-yl]-N-phenylamine was deposited from the vapor onto the hole injecting layer so as to serve as a hole transporting layer having a thickness of 10 nm.

Subsequently, the compound (A-3), which was a naphthacene derivative, as a host material and a compound (C-1) represented by the following formula (7),

[Chemical formula 20]

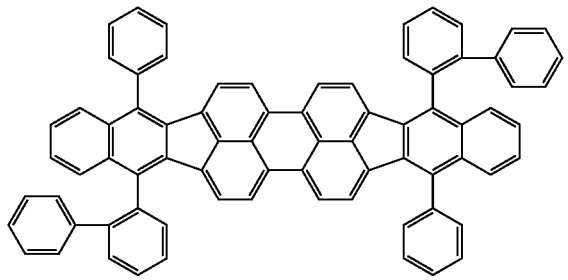

(7)

which was a perifuranthene derivative, as a dopant were simultaneously deposited from the vapor at a mass ratio "(A-3):(C-1)" of 40:0.4 onto the hole transporting layer so as to serve as an organic emitting layer having a thickness of 40 nm.

Subsequently, –[4-[10-(naphthalen-2-yl) anthracen-9-yl]-phenyl]-2-phenyl-1H-benzimidazole was deposited from the vapor onto the organic emitting layer so as to serve as an electron transporting layer having a thickness of 30 nm.

Subsequently, lithium fluoride was deposited from the vapor onto the electron transporting layer so as to have a thickness of 1 nm, and then aluminum was deposited from the vapor onto lithium fluoride so as to have a thickness of 150 nm. The aluminum/lithium fluoride layer functions as a cathode. Thus, the organic EL device of the present invention was produced.

The resultant device was subjected to a current test. As a result, at a current density of 10 mA/cm$^2$, the device was driven at a voltage of 4.4 V, and emitted red light having a luminance of 1,072 cd/m$^2$. The emitted light had chromaticity coordinates of (0.67, 0.33), and the device had a current efficiency of 10.7 cd/A. In addition, the device was subjected to a DC continuous current test at an initial luminance of 10,000 cd/m$^2$. As a result, the time period for which the device was driven so that its luminance reached 80% of the initial luminance was 2,000 hours.

Example 2

The organic EL device of the present invention was produced in the same manner as in Example 1 except that a material obtained by adding the diol compound B-3 to the compound A-3 was used. The concentration of the diol compound in the material in the case was 0.04% by mass.

The resultant device was subjected to a current test. As a result, at a current density of 10 mA/cm$^2$, the device was driven at a voltage of 4.4 V, and emitted red light having a luminance of 1,056 cd/m$^2$. The emitted light had chromaticity coordinates of (0.67, 0.33), and the device had a current efficiency of 10.6 cd/A. In addition, the device was subjected to a DC continuous current test at an initial luminance of 10,000 cd/m$^2$. As a result, the time period for which the device was driven so that its luminance reached 80% of the initial luminance was 800 hours.

Example 3

The organic EL device of the present invention was produced in the same manner as in Example 1 except that a material obtained by adding the diol compound B-3 to the compound A-3 was used. The concentration of the diol compound in the material in the case was 0.11% by mass.

The resultant device was subjected to a current test. As a result, at a current density of 10 mA/cm$^2$, the device was driven at a voltage of 4.2 V, and emitted red light having a luminance of 1,087 cd/m$^2$. The emitted light had chromaticity coordinates of (0.67, 0.33), and the device had a current efficiency of 10.9 cd/A. In addition, the device was subjected to a DC continuous current test at an initial luminance of 10,000 cd/m$^2$. As a result, the time period for which the device was driven so that its luminance reached 80% of the initial luminance was 1,000 hours.

Comparative Example 1

An organic EL device for comparison was produced in the same manner as in Example 1 except that a material obtained by adding the diol compound B-3 to the compound A-3 was used. The concentration of the diol compound in the material in the case was 0.16% by mass.

The resultant device was subjected to a current test. As a result, at a current density of 10 mA/cm$^2$, the device was driven at a voltage of 4.3 V, and emitted red light having a luminance of 1,059 cd/m$^2$. The emitted light had chromaticity coordinates of (0.67, 0.33), and the device had a current efficiency of 10.6 cd/A. In addition, the device was subjected to a DC continuous current test at an initial luminance of 10,000 cd/m$^2$. As a result, the time period for which the device was driven so that its luminance reached 80% of the initial luminance was 200 hours.

Comparative Example 2

An organic EL device for comparison was produced in the same manner as in Example 1 except that a material obtained by adding the diol compound B-3 to the compound A-3 was used. The concentration of the diol compound in the material in the case was 0.30% by mass.

The resultant device was subjected to a current test. As a result, at a current density of 10 mA/cm², the device was driven at a voltage of 4.4 V, and emitted red light having a luminance of 1,052 cd/m². The emitted light had chromaticity coordinates of (0.67, 0.33), and the device had a current efficiency of 10.5 cd/A. In addition, the device was subjected to a DC continuous current test at an initial luminance of 10,000 cd/m². As a result, the time period for which the device was driven so that its luminance reached 80% of the initial luminance was 110 hours.

Comparative Example 3

An organic EL device for comparison was produced in the same manner as in Example 1 except that a material obtained by adding the diol compound B-3 to the compound A-3 was used. The concentration of the diol compound in the material in the case was 0.53% by mass.

The resultant device was subjected to a current test. As a result, at a current density of 10 mA/cm², the device was driven at a voltage of 4.4 V, and emitted red light having a luminance of 1,042 cd/m². The emitted light had chromaticity coordinates of (0.67, 0.33), and the device had a current efficiency of 10.4 cd/A. In addition, the device was subjected to a DC continuous current test at an initial luminance of 10,000 cd/m². As a result, the time period for which the device was driven so that its luminance reached 80% of the initial luminance was 63 hours.

Comparative Example 4

An organic EL device for comparison was produced in the same manner as in Example 1 except that a material obtained by adding the diol compound B-3 to the compound A-3 was used. The concentration of the diol compound in the material in the case was 0.80% by mass.

The resultant device was subjected to a current test. As a result, at a current density of 10 mA/cm², the device was driven at a voltage of 4.4 V, and emitted red light having a luminance of 1,048 cd/m². The emitted light had chromaticity coordinates of (0.67, 0.33), and the device had a current efficiency of 10.5 cd/A. In addition, the device was subjected to a DC continuous current test at an initial luminance of 10,000 cd/m². As a result, the time period for which the device was driven so that its luminance reached 80% of the initial luminance was 34 hours.

Comparative Example 5

An organic EL device for comparison was produced in the same manner as in Example 1 except that a material obtained by adding the diol compound B-3 to the compound A-3 was used. The concentration of the diol compound in the material in the case was 0.97% by mass.

The resultant device was subjected to a current test. As a result, at a current density of 10 mA/cm², the device was driven at a voltage of 4.3 V, and emitted red light having a luminance of 1,023 cd/m². The emitted light had chromaticity coordinates of (0.67, 0.33), and the device had a current efficiency of 10.2 cd/A. In addition, the device was subjected to a DC continuous current test at an initial luminance of 10,000 cd/m². As a result, the time period for which the device was driven so that its luminance reached 80% of the initial luminance was 30 hours.

Table 2 shows the voltage at which each of the organic EL devices of Examples 1 to 3 and Comparative Examples 1 to 5 is driven at a current density of 10 mA/cm², the current efficiency of each of the devices at the current density, the chromaticity coordinates of light emitted from each of the devices at the current density, and the time period for which each of the devices is driven so that the luminance of the device reaches 80% of an initial luminance of 10,000 cd/m² (80%-reached time). FIG. 1 shows a graph obtained by plotting the time period for which each of the devices is driven so that the luminance of the device reaches 80% of an initial luminance of 10,000 cd/m² (80%-reached time) indicated by an axis of ordinate versus the concentration of the diol compound in each of the devices (% by mass) indicated by an axis of abscissa.

Table 2 and FIG. 1 showed that each of the organic EL devices of Examples 1 to 3 each having a concentration of a diol compound of less than 0.15% by mass had an 80%-reached time four or more times as long as that of each of the organic EL devices of Comparative Examples 1 to 5.

TABLE 2

| | Organic compound | Hydroxyl group-containing compound | Content of B-3 (% by mass) | Dopant | Voltage at which organic EL device is driven (V) | Chromaticity coordinates | Current efficiency (cd/A) | 80% lifetime (hours) |
|---|---|---|---|---|---|---|---|---|
| Example 1 | A-3 | | 0 | C-1 | 4.4 | (0.67, 0.33) | 10.7 | 2,000 |
| Example 2 | A-3 | B-3 | 0.04 | C-1 | 4.4 | (0.67, 0.33) | 10.6 | 800 |
| Example 3 | A-3 | B-3 | 0.11 | C-1 | 4.2 | (0.67, 0.33) | 10.9 | 1,000 |
| Comparative Example 1 | A-3 | B-3 | 0.16 | C-1 | 4.3 | (0.67, 0.33) | 10.6 | 200 |
| Comparative Example 2 | A-3 | B-3 | 0.30 | C-1 | 4.4 | (0.67, 0.33) | 10.5 | 110 |
| Comparative Example 3 | A-3 | B-3 | 0.53 | C-1 | 4.4 | (0.67, 0.33) | 10.5 | 63 |
| Comparative Example 4 | A-3 | B-3 | 0.80 | C-1 | 4.4 | (0.67, 0.33) | 10.4 | 34 |
| Comparative Example 5 | A-3 | B-3 | 0.97 | C-1 | 4.3 | (0.67, 0.33) | 10.2 | 30 |

Example 4

The organic EL device of the present invention was produced in the same manner as in Example 1 except that the compound (A-3), which was a naphthacene derivative, as a host material in an organic emitting layer and a compound (C-2) represented by the following formula (8), which was a fluoranthene derivative, as a dopant in the layer were simultaneously deposited from the vapor at a mass ratio "(A-3):(C-2)" of 40:2 so as to have a thickness of 40 nm.

[Chemical formula 21]

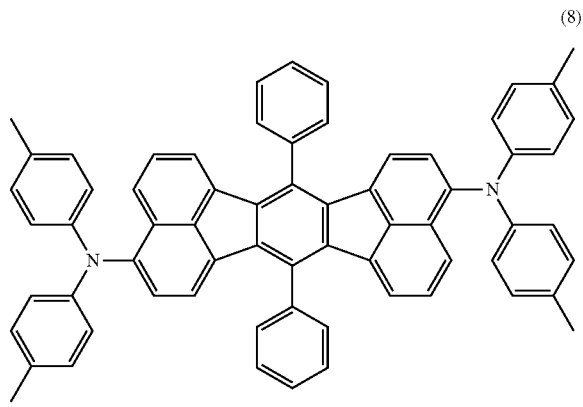

(8)

The resultant device was subjected to a current test. As a result, at a current density of 10 mA/cm$^2$, the device was driven at a voltage of 4.1 V, and emitted orange light having a luminance of 1,161 cd/m$^2$. The emitted light had chromaticity coordinates of (0.58, 0.42), and the device had a current efficiency of 11.6 cd/A. In addition, the device was subjected to a DC continuous current test at an initial luminance of 10,000 cd/m$^2$. As a result, the time period for which the device was driven so that its luminance reached 50% of the initial luminance was 666 hours.

Example 5

The organic EL device of the present invention was produced in the same manner as in Example 4 except that a material obtained by adding the diol compound B-3 to the compound A-3 was used. The concentration of the diol compound in the material in the case was 0.04% by mass.

The resultant device was subjected to a current test. As a result, at a current density of 10 mA/cm$^2$, the device was driven at a voltage of 4.1 V, and emitted orange light having a luminance of 1,186 cd/m$^2$. The emitted light had chromaticity coordinates of (0.58, 0.42), and the device had a current efficiency of 11.9 cd/A. In addition, the device was subjected to a DC continuous current test at an initial luminance of 10,000 cd/m$^2$. As a result, the time period for which the device was driven so that its luminance reached 50% of the initial luminance was 511 hours.

Example 6

The organic EL device of the present invention was produced in the same manner as in Example 4 except that a material obtained by adding the diol compound B-3 to the compound A-3 was used. The concentration of the diol compound in the material in the case was 0.11% by mass.

The resultant device was subjected to a current test. As a result, at a current density of 10 mA/cm$^2$, the device was driven at a voltage of 4.1 V, and emitted orange light having a luminance of 1,145 cd/m$^2$. The emitted light had chromaticity coordinates of (0.58, 0.42), and the device had a current efficiency of 11.5 cd/A. In addition, the device was subjected to a DC continuous current test at an initial luminance of 10,000 cd/m$^2$. As a result, the time period for which the device was driven so that its luminance reached 50% of the initial luminance was 377 hours.

Comparative Example 6

An organic EL device for comparison was produced in the same manner as in Example 4 except that a material obtained by adding the diol compound B-3 to the compound A-3 was used. The concentration of the diol compound in the material in the case was 0.16% by mass.

The resultant device was subjected to a current test. As a result, at a current density of 10 mA/cm$^2$, the device was driven at a voltage of 4.1 V, and emitted orange light having a luminance of 1,091 cd/m$^2$. The emitted light had chromaticity coordinates of (0.58, 0.42), and the device had a current efficiency of 10.9 cd/A. In addition, the device was subjected to a DC continuous current test at an initial luminance of 10,000 cd/m$^2$. As a result, the time period for which the device was driven so that its luminance reached 50% of the initial luminance was 131 hours.

Comparative Example 7

An organic EL device for comparison was produced in the same manner as in Example 4 except that a material obtained by adding the diol compound B-3 to the compound A-3 was used. The concentration of the diol compound in the material in the case was 0.30% by mass.

The resultant device was subjected to a current test. As a result, at a current density of 10 mA/cm$^2$, the device was driven at a voltage of 4.1 V, and emitted orange light having a luminance of 1,171 cd/m$^2$. The emitted light had chromaticity coordinates of (0.58, 0.42), and the device had a current efficiency of 11.7 cd/A. In addition, the device was subjected to a DC continuous current test at an initial luminance of 10,000 cd/m$^2$. As a result, the time period for which the device was driven so that its luminance reached 50% of the initial luminance was 114 hours.

Comparative Example 8

An organic EL device for comparison was produced in the same manner as in Example 4 except that a material obtained by adding the diol compound B-3 to the compound A-3 was used. The concentration of the diol compound in the material in the case was 0.53% by mass.

The resultant device was subjected to a current test. As a result, at a current density of 10 mA/cm$^2$, the device was driven at a voltage of 4.1 V, and emitted orange light having a luminance of 1,139 cd/m$^2$. The emitted light had chromaticity coordinates of (0.58, 0.42), and the device had a current efficiency of 11.4 cd/A. In addition, the device was subjected to a DC continuous current test at an initial luminance of 10,000 cd/m$^2$. As a result, the time period for which the device was driven so that its luminance reached 50% of the initial luminance was 94 hours.

Comparative Example 9

An organic EL device for comparison was produced in the same manner as in Example 4 except that a material obtained by adding the diol compound B-3 to the compound A-3 was used. The concentration of the diol compound in the material in the case was 0.80% by mass.

The resultant device was subjected to a current test. As a result, at a current density of 10 mA/cm$^2$, the device was driven at a voltage of 4.1 V, and emitted orange light having a luminance of 1,146 cd/m². The emitted light had chromaticity coordinates of (0.58, 0.42), and the device had a current efficiency of 11.5 cd/A. In addition, the device was subjected to a DC continuous current test at an initial luminance of 10,000 cd/m². As a result, the time period for which the device was driven so that its luminance reached 50% of the initial luminance was 70 hours.

Comparative Example 10

An organic EL device for comparison was produced in the same manner as in Example 4 except that a material obtained by adding the diol compound B-3 to the compound A-3 was used. The concentration of the diol compound in the material in the case was 0.97% by mass.

The resultant device was subjected to a current test. As a result, at a current density of 10 mA/cm², the device was driven at a voltage of 4.2 V, and emitted orange light having a luminance of 1,194 cd/m². The emitted light had chromaticity coordinates of (0.58, 0.42), and the device had a current efficiency of 11.9 cd/A. In addition, the device was subjected to a DC continuous current test at an initial luminance of 10,000 cd/m². As a result, the time period for which the device was driven so that its luminance reached 50% of the initial luminance was 52 hours.

Figure 2:
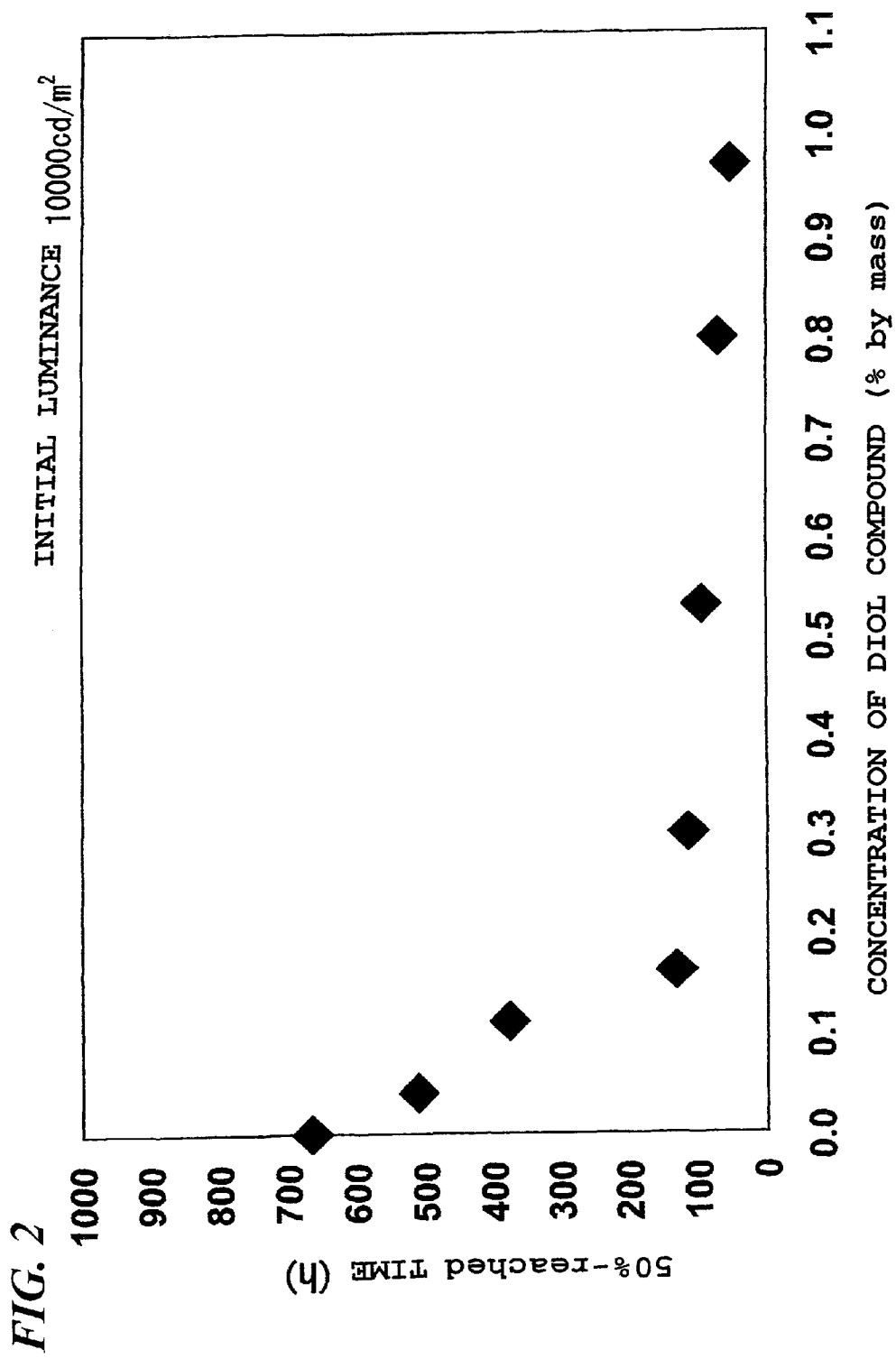
FIG. 2 is a graph obtained by plotting the time period for which each of organic EL devices obtained in Examples 4 to 6 and Comparative Examples 6 to 10 is driven so that the luminance of the device reaches 50% of an initial luminance of 10,000 cd/m² (50%-reached time).

Table 3 shows the voltage at which each of the organic EL devices of Examples 4 to 6 and Comparative Examples 6 to 10 is driven at a current density of 10 mA/cm², the current efficiency of each of the devices at the current density, the chromaticity coordinates of light emitted from each of the devices at the current density, and the time period for which each of the devices is driven so that the luminance of the device reaches 50% of an initial luminance of 10,000 cd/m² (50%-reached time). FIG. 2 shows a graph obtained by plotting the time period for which each of the devices is driven so that the luminance of the device reaches 50% of an initial luminance of 10,000 cd/m² (50%-reached time) indicated by an axis of ordinate versus concentration of the diol compound in each of the devices (% by mass) indicated by an axis of abscissa.

Table 3 and FIG. 2 showed that each of the organic EL devices of Examples 4 to 6 each having a concentration of the diol compound of less than 0.15% by mass had an 50%-reached time three or more times as long as that of each of the organic EL devices of Comparative Examples 6 to 10.

Example 7

Synthesis Example 2

A naphthacene derivative (compound AA-1) was synthesized via the following route.

[Chemical formula 22]

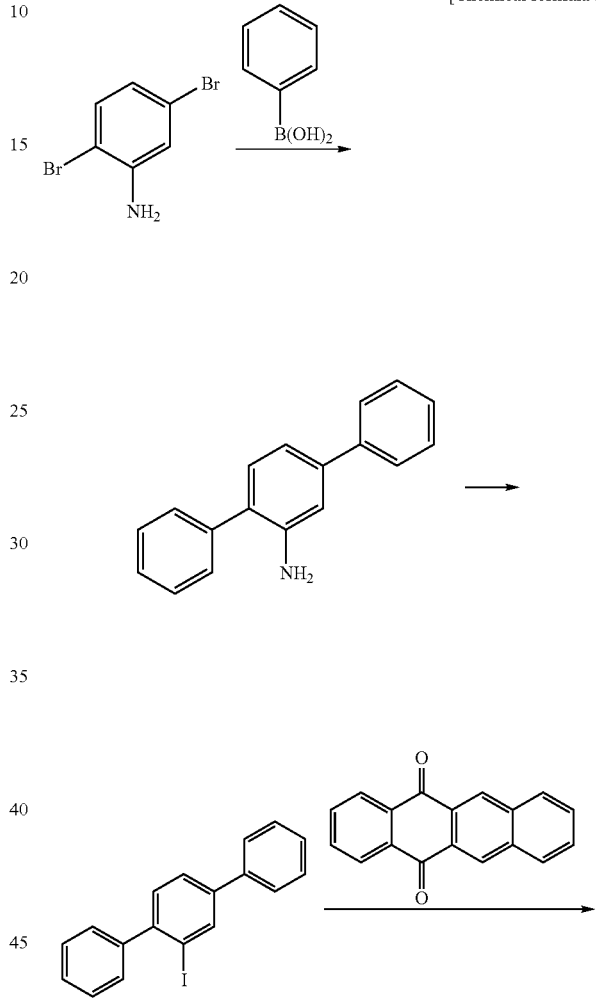

TABLE 3

| | Organic compound | Hydroxyl group-containing compound | Content of B-3 (% by mass) | Dopant | Voltage at which organic EL device is driven (V) | Chromaticity coordinates | Current efficiency (cd/A) | 50% lifetime (hours) |
|---|---|---|---|---|---|---|---|---|
| Example 4 | A-3 | | 0 | C-2 | 4.1 | (0.58, 0.42) | 11.6 | 666 |
| Example 5 | A-3 | B-3 | 0.04 | C-2 | 4.1 | (0.58, 0.42) | 11.9 | 511 |
| Example 6 | A-3 | B-3 | 0.11 | C-2 | 4.1 | (0.58, 0.42) | 11.5 | 377 |
| Comparative Example 6 | A-3 | B-3 | 0.16 | C-2 | 4.1 | (0.58, 0.42) | 10.9 | 131 |
| Comparative Example 7 | A-3 | B-3 | 0.30 | C-2 | 4.1 | (0.58, 0.42) | 11.7 | 114 |
| Comparative Example 8 | A-3 | B-3 | 0.53 | C-2 | 4.1 | (0.58, 0.42) | 11.4 | 94 |
| Comparative Example 9 | A-3 | B-3 | 0.80 | C-2 | 4.1 | (0.58, 0.42) | 11.5 | 70 |
| Comparative Example 10 | A-3 | B-3 | 0.97 | C-2 | 4.2 | (0.58, 0.42) | 11.9 | 52 |

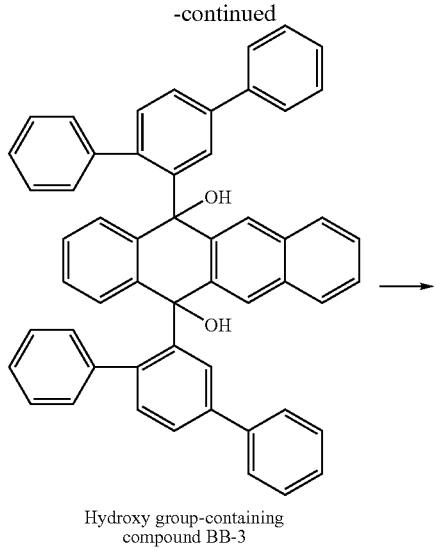

Hydroxy group-containing compound BB-3

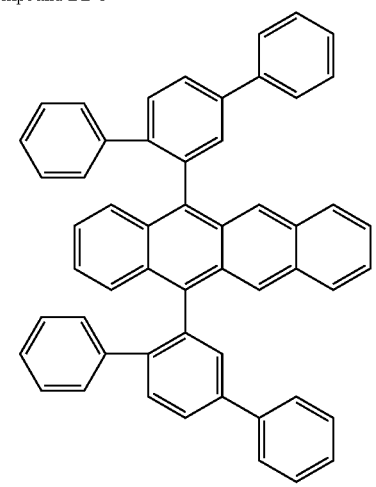

Organic Compound AA-1

Synthesis of 2,5-diphenylaniline 2,5-dibromoaniline (50 g, 199.27 mmol, 1.0 equivalent), phenylboronic acid (58.31 g, 478.25 mmol, 2.4 equivalents), tetrakis(triphenylphosphine)palladium(0) (6.91 g, 5.98 mmol, 0.03 equivalent), sodium carbonate (238.48 g), dimethyl ether (750 milliliters), and water (750 milliliters) were loaded, and the mixture was refluxed for 7 hours. After that, the precipitate was separated by filtration and removed, and ethyl acetate was added to the resultant reaction solution so that an organic layer was extracted. The extracted organic layer was washed with a saturated salt solution, dried with anhydrous sodium sulfate, and concentrated. The resultant residue was purified by short column chromatography (methylene chloride) and silica gel chromatography (methylene chloride:hexane=1:1→2:1). An appropriate amount of hexane was added to the purified residue, and the resultant precipitate was separated by filtration. The resultant precipitate was dried, whereby a white solid was obtained (39.4 g, yield: 81%).

Synthesis of 2,5-diphenyliodobenzene 3N hydrochloric acid (300 milliliters) was added to 2,5-diphenylanilin obtained in the foregoing (25 g, 101.91 mmol, 1.0 equivalent), and the mixture was stirred at 80° C. for 2.5 hours. After that, the mixture was cooled to room temperature. After that, the mixture was further cooled to 5° C. While the temperature of the mixture was kept at 10° C. or lower (5 to 8° C.), an aqueous solution of sodium nitrite (NaNO$_2$: 8.43 g, 122.29 mmol, 1.2 equivalents, H$_2$O: 60 milliliters) was slowly added to the mixture, and the whole was stirred for 0.5 hour. The reaction liquid was dropped into an aqueous solution of potassium iodide (KI: 60.9 g, 366.87 mmol, 3.6 equivalents, H$_2$O: 180 milliliters). An appropriate amount of methylene chloride was further added to the mixture so that a reaction was completed, and the whole was stirred for 0.75 hour at room temperature. Sodium hydrogen dithionite was added to the reaction liquid until the color of the reaction liquid was turned into a yellow color. After that, the mixture was stirred for 0.5 hour, and the organic layer of the resultant reaction liquid was extracted. The extracted organic layer was washed with a saturated salt solution, dried with anhydrous sodium sulfate, and concentrated. The resultant residue was purified by short column chromatography (methylene chloride) and silica gel chromatography (methylene chloride:hexane=1:1→2:1), and the purified residue was dried, whereby a pale pink solid was obtained (24.35 g, yield: 67%).

Synthesis of hydroxyl group-containing compound BB-3 (5,12-bis-(2,5-diphenylbenzo)naphthacene-5, 12-diol)

Under an argon atmosphere, 2,5-diphenyliodobenzene (17.44 g, 48.96 mmol, 2.4 equivalents), dry toluene (150 milliliters), and dry diethyl ether (50 milliliters) were loaded, and the mixture was cooled to −70° C. A solution of n-butyllithium in hexane (1.6 M, 31 milliliters, 48.96 mmol, 2.4 equivalents) was dropped to the mixed liquid, and the whole was stirred for 1 hour while its temperature was slowly increased to −10° C. After the stirring, the reaction solution was cooled to −70° C. again. Then, 5,12-naphthacenequinone (5.27 g, 20.4 mmol, 1.0 equivalent) was added in the form of a solid to the reaction solution, and the mixture was stirred for 2.5 hours while its temperature was slowly increased to room temperature. Methanol (100 milliliters) was added to the reaction liquid, and the mixture was quenched. Then, the resultant precipitate was separated by filtration. The resultant precipitate was washed until its blue color disappeared. Toluene (300 milliliters) was added to the washed precipitate, and the mixture was refluxed for 0.5 hour. The refluxed reaction liquid was cooled to room temperature. After that, the resultant precipitate was separated by filtration, and was washed until its blue color disappeared. Toluene (300 milliliters) was added to the washed precipitate again, and the mixture was repeatedly subjected to a series of operations consisting of reflux, separation by filtration, and washing twice. The resultant precipitate was dried, whereby a white solid was obtained (11.03 g, yield: 75%).

Synthesis of compound AA-1 (5,12-bis-(2,5-diphenylbenzo) naphthacene)

Tetrahydrofuran (600 milliliters) was added to the resultant hydroxyl group-containing compound BB-3 (10 g, 13.9 mmol, 1.0 equivalent), and the mixture was refluxed for 0.25 hour while being bubbled with an argon gas. A solution of stannous chloride dihydrate (31.4 g, 139 mmol, 10 equivalents) in concentrated hydrochloric acid (110 milliliters, 90 equivalents) was dropped to the mixed liquid, and the whole was refluxed for an additional 2 hours. The resultant reaction liquid was dropped to water (1 L), and the resultant precipitate was separated by filtration. The resultant precipitate was washed with 3N hydrochloric acid, water, methanol, and acetone sequentially, and was dried. The washed precipitate was purified by short column chromatography (toluene) and silica gel chromatography (toluene:hexane=1:10→1:3). Acetone was added to the purified product, and the precipitate was separated by filtration. The resultant precipitate was dried, whereby a compound AA-1 as a fluorescent yellow solid was obtained (7.82 g, yield: 82%).

A compound obtained by subjecting the compound AA-1 to sublimation purification at 320 to 340° C. and $5\times10^{-4}$ Pa was represented by AA-2.

Subsequently, a compound obtained by subjecting the compound AA-2 to sublimation purification at 320 to 340° C. and $5\times10^{-4}$ Pa again was represented by AA-3. The concentration of the diol compound in the compound AA-3 was equal to or lower than a detection limit.

The concentration of the diol compound in each of the compounds was analyzed with a high performance liquid chromatograph (HPLC)

Examples 7 to 9 and Comparative Examples 11 to 15

An organic EL device produced by the method of forming a thin film of the present invention was tested for its lifetime as described below.

In each of Examples 1 to 3 and Comparative Examples 1 to 5, the compound AA-3 was used instead of the organic compound A-3, and the compound BB-3 was used instead of the hydroxyl group-containing compound B-3. An ink having a concentration of 1% was prepared by dissolving the compounds AA-3, BB-3, and C-1 in toluene.

A glass substrate measuring 25 mm wide by 75 mm long by 1.1 mm thick and provided with an ITO transparent electrode (manufactured by GEOMATEC Co., Ltd.) was subjected to ultrasonic cleaning in isopropyl alcohol for 5 minutes. After that, the substrate was subjected to ultraviolet light (UV)-ozone cleaning for 30 minutes.

Polyethylenedioxythiophene/polystyrene sulfonate (PEDOT-PSS) to be used as a hole injecting layer was formed into a film having a thickness of 50 nm by a spin coating method on the glass substrate provided with the ITO transparent electrode after the washing, and the resultant was dried under heat on a hot plate at 200° C. for 15 minutes.

After that, the above substrate was brought in a glove box, and was dried under heat at 200° C. for 15 minutes again. Subsequently, a solution of "Polymer 1" (Mw: 145,000) represented by the following formula in toluene (having a solid content of 0.6% by mass) was formed into a film having a thickness of 20 nm by a spin coating method on the substrate, and the resultant was dried under heat on a hot plate at 170° C. for 30 minutes. Subsequently, the prepared organic EL material-containing ink was formed into a film having a thickness of 40 nm by a spin coating method on the film of Polymer 1, and the resultant was dried under heat on a hot plate at 120° C. for 30 minutes.

After that, the above substrate was conveyed to a vacuum deposition chamber via a chamber linked to the glove box. Tris(8-quinolinol) aluminum was deposited from the vapor onto the substrate so as to serve as an electron injecting layer having a thickness of 20 nm. LiF was deposited from the vapor onto the layer so as to serve as an inorganic film having a thickness of 0.2 nm, and aluminum was deposited from the vapor onto the film so as to serve as a cathode having a thickness of 100 nm, whereby an organic EL device was produced. A degree of vacuum at the time of the vapor deposition of each layer was $10^{-5}$ Pa. The produced red organic EL device had a uniform emitting surface, and a current efficiency of 5.1 cd/A. The time period for which the device was driven so that its luminance reached 50% of an initial luminance of 1,000 cd/m² (50%-reached time) was 3,500 hours.

[Chemical formula 23]

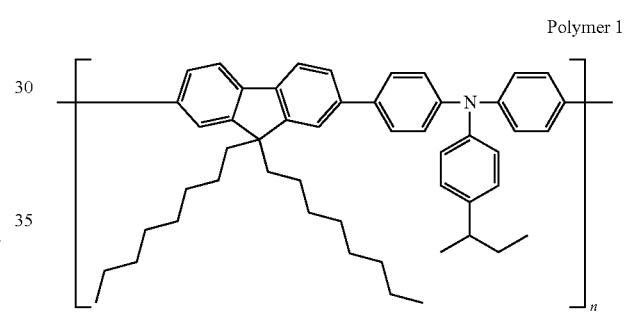

Polymer 1

Figure 3:
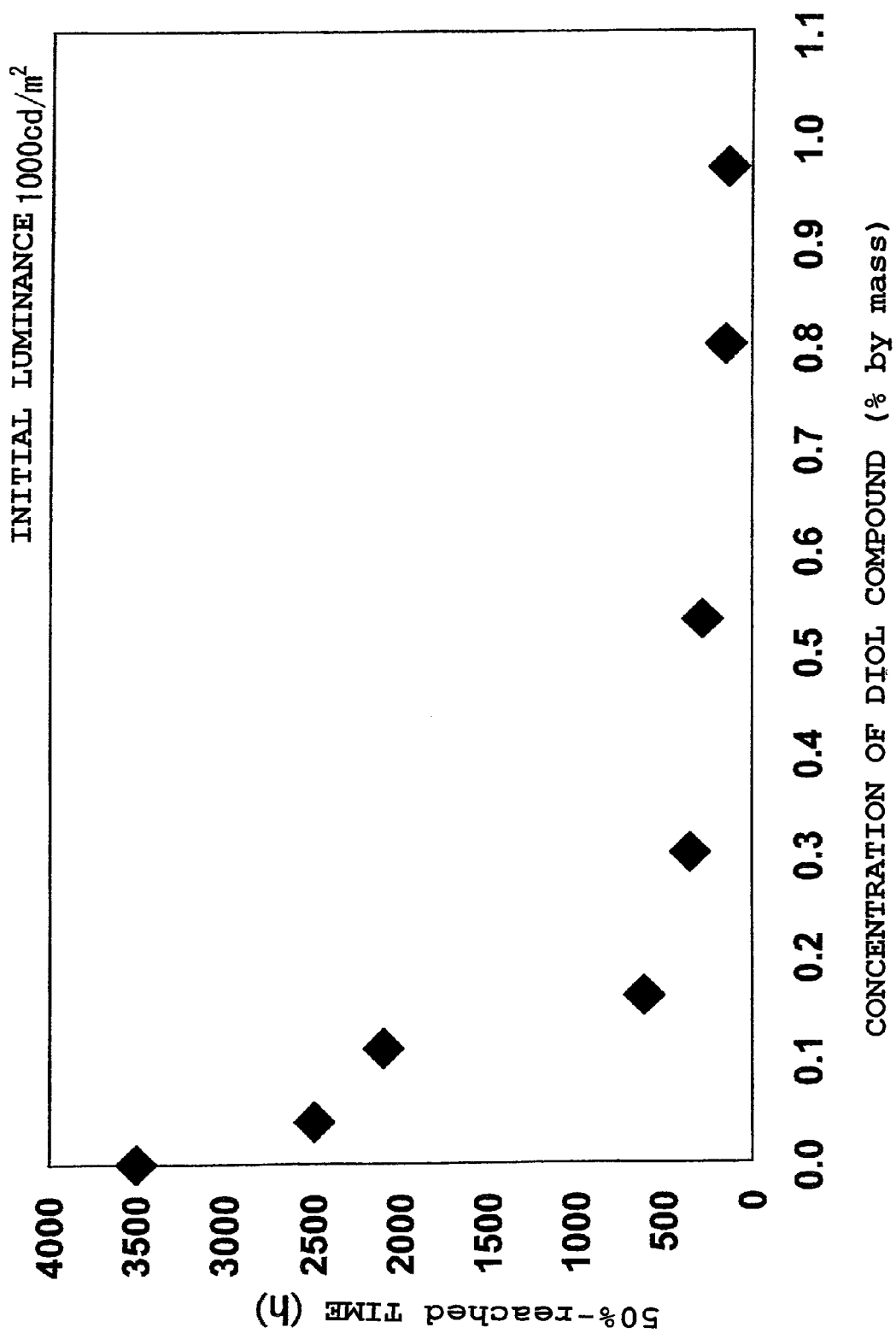
FIG. 3 is a graph obtained by plotting the time period for which each of organic EL devices obtained in Examples 7 to 9 and Comparative Examples 11 to 15 is driven so that the luminance of the device reaches 50% of an initial luminance of 1,000 cd/m² (50%-reached time).

Table 3 summarizes the results of the evaluation of each prepared ink and each produced device, and FIG. 3 shows a graph showing a change in 50%-reached time with a concentration of a diol compound.

TABLE 4

|  | Organic compound | Hydroxyl group-containing compound | Content of B-3 (% by mass) | Dopant | Current efficiency (cd/A) | 50% lifetime (hours) |
| --- | --- | --- | --- | --- | --- | --- |
| Example 7 | AA-3 |  | 0 | C-1 | 5.1 | 3,500 |
| Example 8 | AA-3 | BB-3 | 0.04 | C-1 | 5.0 | 2,500 |
| Example 9 | AA-3 | BB-3 | 0.11 | C-1 | 5.1 | 2,100 |
| Comparative Example 11 | AA-3 | BB-3 | 0.16 | C-1 | 5.1 | 610 |
| Comparative Example 12 | AA-3 | BB-3 | 0.30 | C-1 | 4.9 | 350 |
| Comparative Example 13 | AA-3 | BB-3 | 0.53 | C-1 | 5.0 | 280 |
| Comparative Example 14 | AA-3 | BB-3 | 0.80 | C-1 | 5.0 | 150 |
| Comparative Example 15 | AA-3 | BB-3 | 0.97 | C-1 | 5.0 | 135 |

Table 4 and FIG. 3 showed that each of the organic EL devices of Examples 7 to 9 each having a concentration of a diol compound of less than 0.15% by mass had a 50%-reached time three or more times as long as that of each of the organic EL devices of Comparative Examples 11 to 15. The table and the figure showed that the amount of a hydroxyl group-containing impurity significantly affected the lifetime of even an organic EL device produced by the application method of the present invention.

INDUSTRIAL APPLICABILITY

Reducing the concentration of a specific impurity in an organic compound as in the present invention significantly improves the lifetime of an organic EL device, and allows the device to be suitably used in, for example, a display. The organic EL device of the present invention is applicable to a product requested to show high luminance and high luminous efficiency even at a low voltage. The device is applicable to, for example, a display apparatus, a display, a lighting apparatus, a printer light source, or a backlight for a liquid crystal display apparatus; the device is applicable also to the field of, for example, a sign, a placard, or an interior. The display apparatus is, for example, an energy-saving, high-visibility flat panel display. In addition, when the device is applied to the printer light source, the device can be used as a light source for a laser beam printer.

The invention claimed is:

1. An organic electroluminescence device comprising organic compound layers which comprise an organic emitting layer, the organic compound layers being interposed between at least one pair of electrodes, wherein the organic emitting layer comprises a naphthacene compound represented by the following formula:

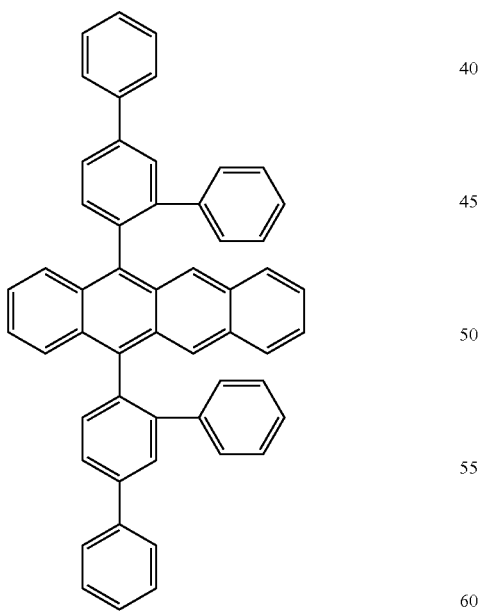

and the naphthacene compound contains less than 0.15% by mass of a hydroxyl group containing compound selected from the group consisting of formula (B-1), (B-2), and (B-3):

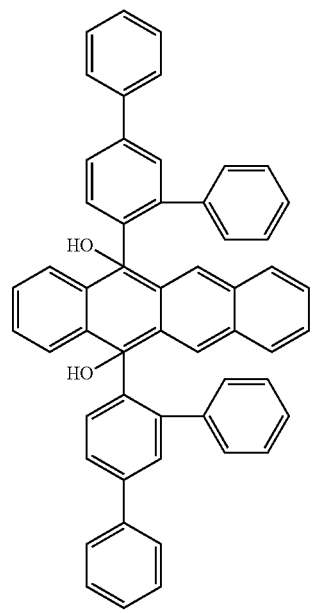

(B-1)

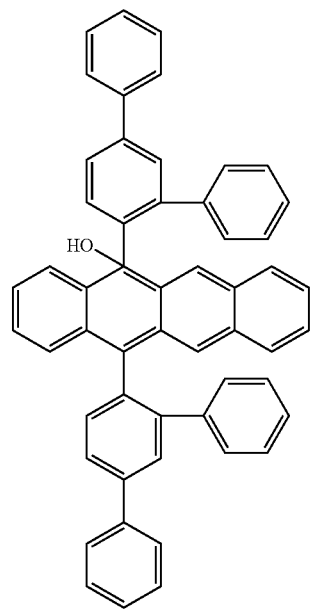 [SMILES: c1ccc(-c2ccc(-c3c4ccccc4c(-c4ccc(-c5ccccc5)cc4-c4ccccc4)c4cc5ccccc5cc34)c(-c3ccccc3)c2)cc1]

(B-2)

(B-3)

2. The organic electroluminescence device according to claim 1, wherein the organic compound layers comprise a hole injecting layer, a hole transporting layer, the organic emitting layer, and an electron injecting layer.

3. The organic electroluminescence device according to claim 1, wherein less than 0.15% by mass of the hydroxyl group-containing compound is achieved by a sublimation method.

4. An organic electroluminescence device according to claim 1, wherein less than 0.15% by mass of the hydroxyl group-containing compound compound is achieved by one of a recrystallization method, a reprecipitation purification method, and a combination of the recrystallization method and the reprecipitation crystallization method.

* * * * *